(12) United States Patent
Campbell et al.

(10) Patent No.: US 6,255,062 B1
(45) Date of Patent: *Jul. 3, 2001

(54) β-TYPE DNA POLYMERASES

(75) Inventors: Judith L. Campbell, Sierra Madre; Martin E. Budd, Pasadena, both of CA (US)

(73) Assignee: California Institute of Technology, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/194,560

(22) Filed: Feb. 14, 1994

(51) Int. Cl.[7] .............................. C12N 9/12; C12N 15/54; C12Q 1/48
(52) U.S. Cl. ........................ 435/15; 435/194; 435/91.1; 435/91.3; 435/91.5; 435/325; 435/320.1; 435/252.3; 536/23.2
(58) Field of Search .................................. 435/194, 91.1, 435/91.3, 91.5, 15, 320.1, 325, 252.3; 536/23.2

(56) References Cited

PUBLICATIONS

Rein, D.C., et al., "DNA Plymerase β: Physiological Roles, Macromolecular Complexes and Accessory Proteins", *Eukayotic Nucleus P.R. Strauss & S.H. Wilson Eds.*, :95–123 (1990).

Bork, P., et al., "What's in a genome?", *Nature* 358: 287 (1992).

Prasad, R., et al., "Yeast open reading frame YCR14C encodes a DNA β– polymerase–like enzyme", *Nucleic Acids Research*, 21(23): 5301–2307 (1993).

Shimizu, K., "Purification and Characterization of a New DNA Polymerase from Budding Yease *Saccharomyces cerevisiae*", *The Journal of Biological Chemistry*, 268(36 of Dec. 25) : 27:48–27:53 (1993).

Sakai, A., "DNA Polymerases of *Tetrahymena pyriformis*. II. Does an N– Ethylmaleimide–Resistant Polymerase Exist in Tetrahymena?", *J. Biochem*, 91: 855–863 (1982).

Sakai, A., "DNA Polymerases of *Tetrahymena pyriformis*. I. Characterization of Two N–Ethylmaleimide–Sensitive DNA Polymerases from Exponentially Growing Cells", *J. Biochem*, 91: 845–853 (1982).

Oliver, S.G., et al., "The Complete DNA sequence of yeast chromosome III", *Nature*, 357: 38–46 (1992).

Wilson, S.H., "Gene Regulation and Structure–Function Studies of Mammalian DNA Polymerase β", *Eukayotic Nucleus P.R., Strauss & S.H. Wilson Eds.*, :199–233 (1990).

Dianov, G. et al., "Generation of Single–Nucleotide Repair Patches Following Excision of Uracil Residues from DNA", *Mol. Cell. Biol.*, 12:1605–1612 (1992).

E.F. Baril et al. "A B–like DNA polymerase Activity in the Slime mold Dictyostelium discoideum" Proc. Natl. Acad. Sci. 77(6) 3317–3321 (Jun. 1980).*

P. Bork et al. "Comprehensive Sequence Analysis of the 182 Predicted Open Reading Frames of Yeast Chromosome III " Protein Science 1:1677–1690 (Dec. 1992).*

* cited by examiner

Primary Examiner—Rebecca E. Prouty
(74) Attorney, Agent, or Firm—Richard F. Trecartin; Flehr Hohbach Test Albritton & Herbert LLP

(57) ABSTRACT

The invention provides novel DNA polymerases of the β-family, called β-type DNA polymerases. Nucleic acids encoding β-type DNA polymerases are provided, as well as expression vectors and host cells containing the nucleic acid encoding the β-type DNA polymerases. The invention further relates to methods for synthesizing nucleic acid using β-type DNA polymerases.

14 Claims, 5 Drawing Sheets

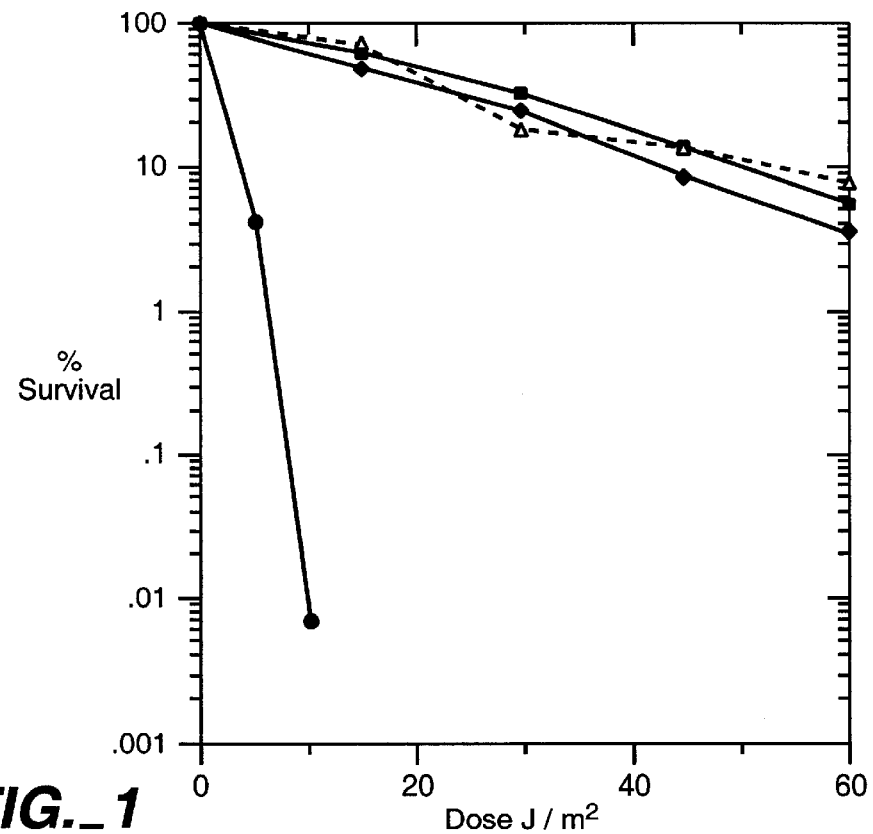
FIG._1
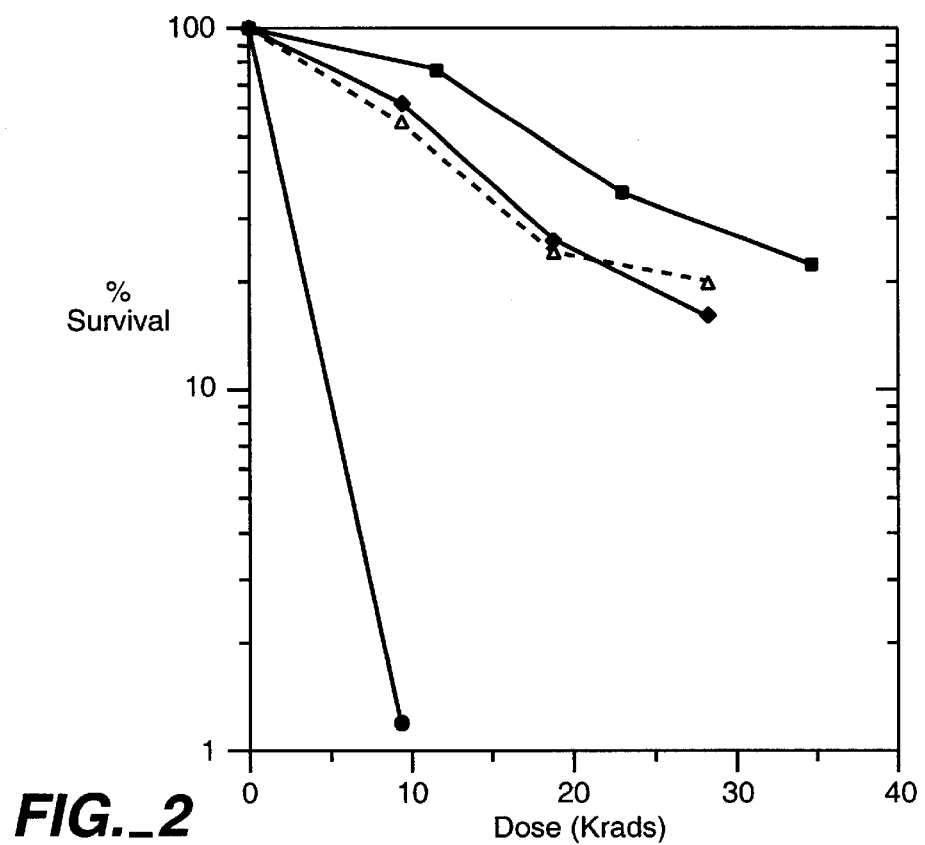
FIG._2

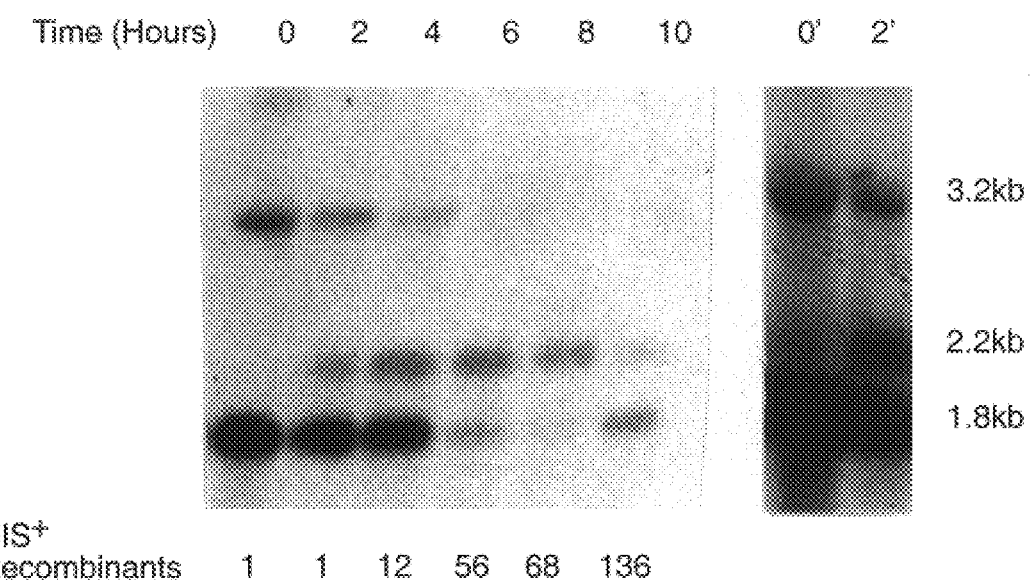
FIG._3

```
   1  ATGTCTCTAA AGGGTAAATT TTTCGCCTTT TTACCTAATC CTAACACATC
  51  TTCCAATAAG TTCTTTAAGA GTATATTGGA GAAAAGGGC GCCACAATTG
 101  TGTCAAGTAT TCAAAATTGT CTTCAATCTA GCCGTAAGGA AGTTATCATT
 151  TTGATTGAGG ACTCCTTTGT TGATTCTGAT ATGCATTTGA CTCAGAAAGA
 201  TATTTTCCAA AGGGAAGCAG GCTTAAATGA TGTCGATGAA TTTCTTGGTA
 251  AGATTGAACA GTCAGGCATT CAATGTGTGA AAACCAGTTG CATCACAAAG
 301  TGGGTCCAGA ATGATAAATT TGCGTTTCAA AAAGATGATT TGATTAAATT
 351  TCAACCATCC ATTATCGTTA TATCAGATAA CGCTGATGAC GGACAAAGTT
 401  CTACTGATAA AGAGAGTGAG ATTTCAACTG ACGTAGAAAG TGAAAGGAAT
 451  GATGACAGCA ACAATAAGGA TATGATACAA GCTTCAAAAC CTCTTAAGCG
 501  ACTTTTACAG GAGGATAAAG GAAGAGCTTC CCTTGTTACT GACAAAACGA
 551  AGTACAAAAA CAATGAATTG ATTATCGGAG CGTTGAAAAG GTTAACAAAA
 601  AAATATGAGA TCGAAGGTGA GAAATTTCGT GCAAGAAGTT ATAGACTGGC
 651  TAAACAGTCG ATGGAAAATT GCGATTTCAA TGTTCGTTCC GGTGAAGAAG
 701  CACATACTAA ATTAAGGAAT ATCGGGCCTA GTATTGCCAA AAAAATACAA
 751  GTTATATTAG ATACGGGAGT TTTACCAGGT TTAAATGATT CAGTGGGATT
 801  AGAAGACAAG TTAAAATACT TCAAAAATTG TTACGGCATT GGGTCGGAAA
 851  TTGCTAAACG CTGGAATCTT CTAAATTTTG AAAGCTTTTG TGTTGCAGCT
 901  AAGAAGGATC CAGAGGAGTT TGTATCAGAT TGGACAATTT TATTTGGTTG
 951  GTCATATTAC GACGATTGGT TATGCAAGAT GTCTCGGAAT GAATGTTTCA
1001  CACATTTAAA GAAGGTTCAA AAAGCGCTGC GTGGCATTGA TCCTGAATGC
1051  CAAGTCGAAT TACAGGGAAG TTATAATAGG GGCTATTCCA AGTGTGGTGA
1101  CATTGATCTT TTATTTTTCA AGCCGTTTTG TAATGACACG ACCGAGTTGG
1151  CAAAAATCAT GGAACGCTT TGTATTAAGT TGTACAAGGA TGGCTATATC
1201  CATTGTTTTT TACAGCTAAC GCCAAACTTG AAAAGCTAT TCTTAAAAAG
1251  AATAGTGGAG AGATTTCGTA CAGCGAAGAT TGTTGGGTAT GGAGAAAGAA
1301  AGAGGTGGTA TTCTTCTGAG ATAATCAAGA AATTTTTCAT GGGAGTCAAA
1351  TTCTCTCCAA GAGAATTAGA AGAACTGAAA GAAATGAAAA ATGATGAAGG
1401  CACATTGTTA ATTGAAGAAG AAGAAGAAGA AGAAACAAAA TTAAACCCGA
1451  TTGACCAATA TATGTCTCTG AATGCCAAGG ATGGAAATTA TTGCAGAAGA
1501  TTAGACTTTT TTTGTTGCAA GTGGGATGAG CTTGGAGCAG GAAGAATACA
1551  CTATACTGGA TCTAAAGAGT ACAATAGATG GATAAGAATA TTGGCAGCGC
1601  AAAAAGGCTT CAAGCTTACA CAACACGGTT TATTTCGAAA TAATATCCTT
1651  CTCGAAAGCT TTAACGAACG CAGAATTTTC GAGTTATTAA ACTTAAAATA
1701  CGCTGAACCC GAACATAGAA ATATCGAATG GGAAAAAAAA ACTGCATAAA
1751  GGCATT
```

FIG._4

```
Met Ser Leu Lys Gly Lys Phe Ala Phe Leu Pro Asn  13
Pro Asn Thr Ser Ser Asn Lys Phe Phe Lys Ser Ile Leu  26
Glu Lys Lys Gly Ala Thr Ile Val Ser Ser Ile Gln Asn  39
Cys Leu Gln Ser Ser Arg Lys Glu Val Ile Ile Leu Ile  52
Glu Asp Ser Phe Val Asp Ser Asp Met His Leu Thr Gln  65
Lys Asp Ile Phe Gln Arg Glu Ala Gly Leu Asn Asp Val  78
Asp Glu Phe Leu Gly Lys Ile Glu Gln Ser Gly Ile Gln  91
Cys Val Lys Thr Ser Cys Ile Thr Lys Trp Val Gln Asn 104
Asp Lys Phe Ala Phe Gln Lys Asp Asp Leu Ile Lys Phe 117
Gln Pro Ser Ile Ile Val Ile Ser Asp Asn Ala Asp Asp 130
Gly Gln Ser Ser Thr Asp Lys Glu Ser Glu Ile Ser Thr 143
Asp Val Glu Ser Glu Arg Asn Asp Asp Ser Asn Asn Lys 156
Asp Met Ile Gln Ala Ser Lys Pro Leu Lys Arg Leu Leu 169
Gln Glu Asp Lys Gly Arg Ala Ser Leu Val Thr Asp Lys 182
Thr Lys Tyr Lys Asn Asn Glu Leu Ile Ile Gly Ala Leu 195
Lys Arg Leu Thr Lys Lys Tyr Glu Ile Glu Gly Glu Lys 208
Phe Arg Ala Arg Ser Tyr Arg Leu Ala Lys Gln Ser Met 221
Glu Asn Cys Asp Phe Asn Val Arg Ser Gly Glu Glu Ala 234
His Thr Lys Leu Arg Asn Ile Gly Pro Ser Ile Ala Lys 247
Lys Ile Gln Val Ile Leu Asp Thr Gly Val Leu Pro Gly 260
Leu Asn Asp Ser Val Gly Leu Glu Asp Lys Leu Lys Tyr 273
Phe Lys Asn Cys Tyr Gly Ile Gly Ser Glu Ile Ala Lys 286
Arg Trp Asn Leu Leu Asn Phe Glu Ser Phe Cys Val Ala 299
Ala Lys Lys Asp Pro Glu Glu Pro Val Ser Asp Trp Thr 312
Ile Leu Phe Gly Trp Ser Tyr Tyr Asp Asp Trp Leu Cys 325
```

FIG._5A

```
Lys Met Ser Arg Asn Glu Cys Thr Thr His Leu Lys Lys 338
Val Gln Lys Ala Leu Arg Gly Ile Asp Pro Glu Cys Gln 351
Val Glu Leu Gln Gly Ser Tyr Asn Arg Gly Tyr Ser Lys 364
Cys Gly Asp Ile Asp Leu Leu Phe Phe Lys Pro Phe Cys 377
Asn Asp Thr Thr Glu Leu Ala Lys Ile Met Glu Thr Leu 390
Cys Ile Lys Leu Tyr Lys Asp Gly Tyr Ile His Cys Phe 403
Leu Gln Leu Thr Pro Asn Leu Glu Lys Leu Phe Leu Lys 416
Arg Ile Val Glu Arg Phe Arg Thr Ala Lys Ile Val Gly 429
Tyr Gly Glu Arg Lys Arg Trp Tyr Ser Ser Glu Ile Ile 442
Lys Lys Phe Phe Met Gly Val Lys Phe Ser Pro Arg Glu 455
Leu Glu Glu Leu Lys Glu Met Lys Asn Asp Glu Gly Thr 468
Leu Leu Ile Glu Glu Glu Glu Glu Glu Thr Lys Leu 482
Asn Pro Ile Asp Gln Tyr Met Ser Leu Asn Ala Lys Asp 495
Gly Asn Tyr Cys Arg Arg Leu Asp Phe Phe Cys Cys Lys 508
Trp Asp Glu Leu Gly Ala Gly Arg Ile His Tyr Thr Gly 521
Ser Lys Glu Tyr Asn Arg Trp Ile Arg Ile Leu Ala Ala 534
Gln Lys Gly Phe Lys Leu Thr Gln His Gly Leu Phe Arg 547
Asn Asn Ile Leu Leu Glu Ser Phe Asn Glu Arg Arg Ile 560
Phe Glu Leu Leu Asn Leu Lys Tyr Ala Glu Pro Glu His 573
Arg Asn Ile Glu Trp Glu Lys Lys Thr Ala             583
```

FIG._5B

β-TYPE DNA POLYMERASES

This invention was made with Government support under Grant Nos. GM25508 and GM47281, awarded by the U.S. Public Health Service, and Grant No. 3RT-0190, awarded by the California Tobacco Related Disease Research Program.

FIELD OF THE INVENTION

The invention relates to novel DNA polymerases of the β-family, called β-type DNA polymerases. Nucleic acids encoding β-type polymerases are also provided, as well as expression vectors and host cells containing the nucleic acid encoding β-type DNA polymerase. The invention further relates to methods for synthesizing nucleic acid using β-type DNA polymerases.

BACKGROUND OF THE INVENTION

Three nuclear DNA polymerases, designated α, δ, and ε, have been identified in *Saccharomyces cerevisiae* (Campbell et al. *Genome Dynamics, Protein Synthesis and Energetic*, J. R. Broach, J. R. Pringle, and E. R. Jones, eds. (1991)). The corresponding genes, POL1 (a.k.a. CDC17), POL2,and POL3 (a.k.a. CDC2), (Johnson et al., *Cell* 43, 369–377 (1985); Pizzagalli et al., *Proc. Natl. Acad. Sci. USA* 85, 3772–3776 (1988); Boulet et al., *EMBO J.* 8, 1849–1854 (1989); Morrison et al., *Cell* 62, 1143–1151 (1990)) have been cloned and sequenced and the effect of mutations in these genes has been studied. The genes contain considerable sequence similarity, including a signature set of six highly conserved stretches in the central part of the proteins, and are often referred to as members of the α-class of DNA polymerases. Failure to synthesize chromosomal sized DNA at the restrictive temperature in temperature sensitive mutants affecting DNA polymerases α, δand ε provides direct evidence that these three distinct polymerases are required during DNA replication (Budd et al., *Moll. Cell. Biol.* 9. 365–367 (1989); Budd et al., *Mol. Cell. Biol.* 13, 496–505 (1993)). It has been proposed, based largely on studies in the simian virus 40 system, that during DNA replication DNA polymerase α initiates synthesis of leading and lagging strand primers with either polδ or ε extending the primers. Another yeast gene, REV3, has significant homology to α-class DNA polymerases (Morrison et al., *J. Bacteriol.* 171, 5659–5667 (1989)). Strains with deletions of the REV3 gene are viable, grow at a normal rate, show decreased induced mutation rates, and are slightly sensitive to UV, suggesting that the REV3 protein functions in mutagenic repair but not replication. However, no DNA polymerase activity corresponding to the REV3 gene has been identified to date.

Yet another nuclear eukaryotic DNA polymerase, DNA polymerase β, has been identified in mammalian cells but not in lower eukaryotes such as yeast (Rein et al., In *The Eukaryotic Nucleus*, P. R. Strauss, and S. H. Wilson, eds. pp. 95–123 (1990); Wilson, In *The Eukaryotic Nucleus*, P. R. Strauss, and S. H. Wilson, eds. pp. 199–233 (1990)). Genes encoding DNA polymerase β have been cloned from several sources, and the sequence of the predicted proteins do not share significant similarity with the α-class. Mammalian DNA polymerase β is a small protein of only 40 kDa, and has received much attention from investigators interested in structure/function relationships in DNA polymerases, because it comprises the minimal functional DNA polymerase domain of any known naturally occurring polymerase. Little is known about its in vivo function, however.

Since DNA polymerase β is expressed in non-mitotic, fully differentiated tissues such as the brain (Zmudzka et al., *Nucleic Acids Research* 16, 9587–9596 (1988); Hirose et al. *Experimental Cell Research* 181, 169–180 (1989); Nowak et al., *Biochem. Biophys. Acta* 1008, 203–207 (1989)), it is believed to play a role in DNA repair rather than DNA replication. In further support of this idea, the replicative polymerase, DNA polymerase α, increases dramatically in liver or human lymphocytes stimulated to undergo DNA synthesis, whereas DNA polymerase β does not (Chang et al.,*J. Mol. Biol.* 74, 1–8 (1973); Bertazzoni et al.,*Proc. Natl. Acad. Sci.* 73, 783–789 (1976)). A role for DNA polymerase β in DNA repair is also suggested by its biochemical properties. DNA polymerase β preferentially catalyzes repair DNA synthesis at small gaps in duplex DNA substrates (Mosbaugh et al., *J. Biol. Chem.* 258, 108–118 (1982); Randahl et al., *J. Biol. Chem.* 263, 12228–12234 (1988); Singhad et al. *J. Biol. Chem.* 268, 15906–15911 (1993)). In HeLa cell extracts, DNA polymerase β repairs the single nucleotide gap created by glycosylase repair of G/T mispairs (Wiebauer et al., *Proc. Natl. Acad. Sci. USA* 87, 5842–5845 (1990)). Similarly, an aphidicolin resistant polymerase in Hela cell extracts repairs a single nucleotide gap created by excision of uracil residues from duplex DNA, implying that mammalian DNA polymerase β, the only known nuclear aphidicolin resistant DNA polymerase, is involved (Dianov et al., *Mol. Cell. Biol.* 12, 1605–1612 (1992)). A replicative function has not been entirely excluded, however, as mammalian DNA polymerase β appears to be required to replicate single stranded DNA injected into Xenopus oocytes (Jenkins et al., *Science* 258, 475–477 (1992)). Also, when expressed in *E. coli*, DNA polymerase β can complement the gap filling deficiency of a DNA polymerase I mutant, perhaps suggesting a role in processing Okazaki fragments (Sweasy et al.,*J. Biol. Chem.* 267 1407–1410 (1992)).

The mammalian DNA polymerase βs share several properties, including low molecular weights (32,000 to 40,000), alkaline pI and pH optima, stimulation by 50–100 mM salt, inhibition by phosphate, resistance to aphidicolin, sensitivity to dideoxythymidine triphosphate, and general resistance to N-ethylmaleimide (NEM). In addition, the β-polymerases are considered to be substantially non-processive, synthesizing only short stretches of DNA in a single binding event to the primed template. β-polymerases also copy RNA as well as DNA templates, although the rat β-polymerase only exhibits reverse transcriptase activity in the presence of Mn++ (Wang et al., Biochemistry 16, 4927–4934 (1977), Ono et al., *Nucleic Acids Research* 7, 715–726 (1979), Yoshida et al.,*J. Biochem.* 85, 1387–1395 (1979)).

In addition, mammalian β-polymerases show the highest error rate measured for cellular DNA polymerases. This may be due to the reduced ability of β-polymerases to discriminate among substrates compared to α polymerases, since they may exhibit up to 20 to 50% of normal activity in the presence of a single dNTP as in the presence of all four dNTPs (Rein et al., supra).

An α-DNA polymerase and a β-DNA polymerase were reported in *Tetrahymena pyriformis*, a protozoa (Sakai et al., J. Biochem. 91, 845–853 (1982); Sakai et al., J. Biochem. 91, 855–863 (1982)). The two polymerases were purified from exponentially growing cells and purified. The β-DNA polymerase had a molecular weight of about 70,000,was inhibited by NEM, resistant to aphidicolin, and could not synthesize DNA in the presence of Mn++.

The complete DNA sequence of the *Saccharomyces cerevisiae* chromosome III has been elucidated as a result of the European yeast genome project (Oliver et al., *Nature* 357:38–46 (1992). Low-stringency homology searching identified an open reading frame (ORF) of 582 amino acids which has 26% homology to rat DNA polymerase-β over the 393 amino acids of the C-terminal portion of the ORF. (Bork et al., *Nature*, 358:287 (1992)).

SUMMARY OF THE INVENTION

It is an object of the invention to provide a new form of DNA polymerase, β-type DNA polymerase, as well as variants of β-type DNA polymerases, and to produce useful quantities of these β-type DNA polymerases using recombinant DNA techniques.

It is a further object of the invention to provide recombinant or isolated nucleic acids encoding β-type DNA polymerases, and expression vectors and host cells containing the nucleic acid encoding the β-type DNA polymerase.

An additional object of the invention is to provide methods for synthesizing nucleic acids and for producing nucleic acids which have synthetic, modified or labelled nucleotides incorporated into the synthesized strand.

In accordance with the foregoing objects, the invention provides recombinant β-type DNA polymerases, and isolated or recombinant nucleic acids which encode the β-type DNA polymerases of the invention. Also provided are expression vectors which comprise DNA encoding a β-type DNA polymerase operably linked to transcriptional and translational regulatory DNA, and host cells which contain such expression vectors.

An additional aspect of the invention provides methods for producing β-type DNA polymerases which comprise culturing a host cell transformed with an expression vector and causing expression of the β-type DNA polymerase encoding expression vector to produce a recombinant β-type DNA polymerase.

A further aspect of the invention provides methods for synthesizing nucleic acids. A nucleic acid primer and a nucleic acid template are contacted to form a primed template, and a recombinant β-type DNA polymerase is added in the presence of a mixture comprising at least one activated adenosine nucleotide, one activated thymidine nucleotide, one activated cytidine nucleotide and one activated guanosine nucleotide. An additional aspect provides a mixture of at least one activated adenosine nucleotide, one activated uridine nucleotide, one activated cytidine nucleotide and one activated guanosine nucleotide.

The invention also provides methods for synthesizing nucleic acids containing base pair mismatches. A nucleic acid primer and a nucleic acid template are contacted to form a primed template, and a recombinant β-type DNA polymerase is added in the presence of at least one activated nucleotide. The sequence of the newly synthesized strand contains one or more base pair mismatches as compared to the sequence of the template.

A further aspect of the invention relates to methods for synthesizing nucleic acid containing at least one modified nucleotide. A nucleic acid primer and a nucleic acid template are contacted to form a primed template, and a recombinant β-type DNA polymerase is added in the presence of at least one activated modified nucleotide. This method also allows the synthesis of labelled nucleic acid through the use of labelled activated nucleotides.

The invention further provides a kit for the synthesis of nucleic acid comprising a recombinant β-type DNA polymerase. Additional kits are provided for the synthesis of nucleic acid with modified nucleotides incorporated therein, wherein the kit comprises a recombinant β-type DNA polymerase and at least one modified activated nucleotide. In some instances, the modified activated nucleotide may be a labelled activated nucleotide, such that the newly synthesized nucleic acid is labelled.

BRIEF DESCRIPTION OF THE DRAWINGS

FIG. 1 depicts the UV survival curve of ■: 6210-4A (POL4+), ♦: 6210-2C (pol4Δ), ▲: 6210-2D (pol4Δ), and ●: X12-6B (rad1-1) strains.

FIG. 2 depicts the X-ray survival curve of ■: D6212 (POL4+/POL4+); ♦: D6213 (pol4Δ/pol4Δ); ▲: D6214 (pol4Δ/pol4Δ); and ●: M754-3-6D (rad 54-3) strains.

FIG. 3 depicts the induction of yeast β-type DNA polymerase message in meiosis. RNA was purified from cells at the indicated times during meiosis, electrophoresed, transferred to Gene Screen (Dupont), and probed with DNA from the POL4 coding region. The numbers below the panel indicate the number of His+ recombinants observed relative to time 0, and indicated commitment to meiotic recombination. Lanes labeled 0' and 2' are the 0 and 2 hour time points exposed long enough to reveal the small amount of POL4 RNA in exponentially growing cells.

FIG. 4 depicts the nucleic acid sequence (SEQ ID NO:1) of the yeast β-type DNA polymerase.

FIGS. 5A and 5B depict the amino acid sequence (SEQ ID NO:2) of the yeast β-type DNA polymerase.

DETAILED DESCRIPTION OF THE INVENTION

The invention provides novel β-type DNA polymerases. The definition of a "β-type DNA polymerase" or a "β-type nucleic acid polymerase" is based primarily on structure. As discussed in more detail hereinafter, β-type DNA polymerases have significant sequence homology to the amino acid sequence (SEQ ID NO:2)of the yeast β-type DNA polymerase as shown in FIG. 5. Likewise, the nucleic acids encoding β-type DNA polymerases have significant sequence homology to the nucleic acid sequence (SEQ ID NO:1) encoding β-type DNA polymerases as shown in FIG. 4.

In some embodiments, the β-type DNA polymerases are functionally similar to the mammalian DNA β-polymerases. However, the level of nucleic acid and amino acid sequence homology between the known β-DNA polymerases and the novel β-type DNA polymerases of the invention is very low, and thus serves as a significant distinguishing factor between the two.

Generally, the β-type DNA polymerases of the invention also have one or more of the following characteristics. First, β-type DNA polymerases are capable of nucleic acid synthesis, as in the replication or repair of nucleic acid. This synthesis can be either of DNA or RNA, or of molecules which contain both deoxyribo- and ribonucleic acids, and may utilize either DNA or RNA primed templates. Furthermore, β-type DNA polymerases are usually both resistant to aphidicolin and sensitive to dideoxynucleoside triphosphate substrates.

In addition, the β-type DNA polymerases of the invention exhibit loose substrate specificity, as evidenced by comparatively efficient incorporation of ddNTPs and even rNTPs, as well as extensive noncomplementary incorporation in the presence of a single dNTP. The β-type DNA polymerase from yeast appears to be the least discriminating of the known DNA polymerases, as outlined below. Due to this loose substrate specificity, β-type DNA polymerases are useful in the synthesis of nucleic acids with modified or labelled nucleotides, as well as nucleic acids with base pair mismatches.

Accordingly, the β-type DNA polymerases of the invention find use in a number of applications. In particular, β-type DNA polymerases are useful as nucleic acid polymerases in the synthesis of nucleic acid. In the broadest embodiment, β-type DNA polymerase is used to synthesize nucleic acid from a primed template, and thus the β-type DNA polymerases of the invention are useful as replacements for other DNA polymerases and RNA polymerases.

Thus, in a preferred embodiment, the β-type nucleic acid polymerases of the present invention are used to generate large amounts of nucleic acid through cycling methods well known in the art.

In alternative embodiments, β-type DNA polymerases are used to synthesize nucleic acid which contains mutations, or base pair mismatches when compared to the template sequence. Thus the β-type DNA polymerases of the invention are useful in the generation of random, site-specific or region-specific nucleic acid mutations.

In a preferred embodiment, β-type DNA polymerase is used to synthesize nucleic acid which contains unconventional nucleotides. For example, synthetic, modified or labelled nucleotides may be incorporated into nucleic acid.

For example, the β-type nucleic acid polymerases of the present invention are useful in the incorporation of new or synthetic bases to form nucleic acids with greater functional diversity. For example, RNA made in this manner may possess greater catalytic potential, and thus β-type DNA polymerases are useful in the creation of ribozymes.

In addition, β-type DNA polymerases are useful as reagents in diagnostic assays for β-type DNA polymerase or antibodies to β-type DNA polymerase, or when insolubilized in accord with known methods as agents for the purification of β-type DNA polymerase antibodies from antisera or hybridoma culture. β-type DNA polymerase is also useful as an immunogen to produce antibodies to β-type DNA polymerase.

The β-type DNA polymerases of the invention are identified and utilized as outlined below.

A β-type DNA polymerase nucleic acid or β-type DNA polymerase protein is initially identified by substantial nucleic acid and/or amino acid sequence homology to the sequences shown in FIGS. 4 (SEQ ID NO:1) and 5 (SEQ ID NO:2). Such homology is based upon the overall nucleic acid or amino acid sequence. In the case of the protein, the overall homology of the protein sequence to the amino acid sequence shown in FIG. 5 (SEQ ID NO:2) is greater than about 50%, preferably greater than about 75%, more preferably greater than about 90% and most preferably greater than about 95–98%. Thus the rat β DNA polymerase, which exhibits a 26% homology to the C-terminal 393 amino acids of the yeast β-type DNA polymerase enzyme, with a corresponding 39% homology on the DNA level, is not a β-type DNA polymerase. In the case of the nucleic acid, the overall homology of the nucleic acid sequence is measured commensurate with the amino acid homology but takes into account the degeneracy of the genetic code and codon bias of different organisms. Accordingly, the nucleic acid sequence homology may be either lower or higher than that of the protein sequence. Thus the homology of the DNA sequence of a β-type DNA polymerase as compared to the DNA sequence of FIG. 4 (SEQ ID NO:1) is preferably greater than 50%, more preferably greater than 60% and most preferably greater than 75%. In some cases, the homology will be greater than about 90%.

The homology of the amino acid and nucleic acid sequence is determined using standard techniques known in the art, such as the Best Fit sequence program described by Devereux et al. *Nucl. Acid Res.* 12:387–395 (1984). The alignment may include the introduction of gaps in the sequences to be aligned. In addition, for sequences which contain either more or fewer residues than the protein or DNA sequence shown in FIGS. 4 (SEQ ID NO:1) and 5 (SEQ ID NO:2), it is understood that the percentage of homology will be determined based on the number of homologous residues in relation to the total number of residues. Thus, for example, homology of sequences shorter than that shown in FIGS. 4 (SEQ ID NO:1) and 5 (SEQ ID NO:2) will be determined using the total number of residues in the shorter sequence.

The β-type DNA polymerase proteins and nucleic acids of the invention are preferably recombinant. As used herein, "nucleic acid" may refer to either DNA or RNA, or molecules which contain both ribo- and deoxyribonucleotides. The nucleic acids include genomic DNA, cDNA and oligonucleotides including sense and anti-sense nucleic acids. The nucleic acid may be double stranded, single stranded, or contain portions of both double stranded or single stranded sequence. The nucleic acid may contain naturally occurring bases, or non-naturally occurring bases, e.g., synthetic, modified or labelled bases or nucleotides. For example, dideoxynucleotides as well as other chain terminators, may be incorporated into the nucleic acids, as well as nucleotides containing novel or unusual sugar moieties. By the term "recombinant nucleic acid" herein is meant nucleic acid in a form not normally found in nature. That is, a recombinant nucleic acid is flanked by a nucleotide sequence not naturally flanking the nucleic acid. Recombinant nucleic acids can originally formed in vitro by the manipulation of nucleic acid by restriction endonucleases, or alternatively using such techniques as polymerase chain reaction. Thus an isolated β-type DNA polymerase gene, in a linear form, or an expression vector formed in vitro by ligating β-type DNA polymerase DNA molecules with a nucleic acid not normally associated with it, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e., through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production of a β-type DNA polymerase from one organism in the same or different organism or host cell. For example, the protein may be made in the same organism from which it is derived but at a significantly higher concentration than is normally seen, e.g., through the use of a inducible or high expression promoter, such that increased levels of the protein is made. Alternatively, the protein may be in a form not normally found in nature, as in the addition of an epitope tag or amino acid substitutions, insertions and deletions.

A β-type DNA polymerase nucleic acid from an organism other than Saccharomyces cerevisiae can be readily identified by standard methods utilizing all or part of the sequence shown in FIG. 4 (SEQ ID NO:1). Classes of organisms from which β-type DNA polymerases may be cloned include eukaryotes and procaryotes. The eukaryotes include higher eukaryotes such as mammals, and lower eukaryotes such as yeast, although generally protozoan β-type DNA polymerases are not preferred.

To this end, labelled probes corresponding to all or part of the sequence shown in FIG. 4 (SEQ ID NO:1) can be used for in situ hybridization to detect the presence of an β-type DNA polymerase gene in a particular organism. In addition, such probes can be used to screen genomic or cDNA libraries or to identify one or more bands containing all or part of the β-type DNA polymerase gene by hybridization to an electrophoretically separated preparation of genomic DNA digested with one or more restriction endonucleases.

The length of the probes will vary depending upon the organism screened and the level of homology. Generally probes may be at least about 10 bases in length, and will generally be no more than about 50 bases in length, with a preferred range of about 15 to 30 bases. However, it is to be understood that much longer probes may be used, comprising all or a significant part of the sequence shown in FIG. 4 (SEQ ID NO:1), for example to clone the S. cerevisiae gene encoding the β-type DNA polymerase.

The hybridization conditions will vary depending upon the probe used, and will be ascertainable by one skilled in the art using routine experimentation. Generally, low stringency conditions, e.g., 4–5×SSC at 50° C., will be used in the initial screening of genomes other than that of yeast. High stringency conditions may also be used, i.e., 0.1×SSC. 0.1% SDS at 65° C., when genes having higher homology are probed. Genes hybridizing to the probe are then sequenced, and the nucleic acid and amino acid sequences compared to the sequences of FIGS. 4 (SEQ ID NO:1) and 5 (SEQ ID NO:2).

Once the β-type DNA polymerase nucleic acid is identified, it can be cloned and, if necessary, its constituent parts recombined to form the entire β-type DNA polymerase nucleic acid. Once isolated from its natural source, e.g., contained within a plasmid or other vector or excised therefrom as a linear nucleic acid segment, the recombinant β-type DNA polymerase nucleic acid can be further used as a probe to identify and isolate other β-type DNA polymerase nucleic acids. It can also be used as a "precursor" nucleic acid to make modified or variant β-type DNA polymerase nucleic acids and proteins, as will be outlined below.

Using the nucleic acids of the invention which encode β-type DNA polymerase, a variety of expression vectors are made. The expression vectors may be either self-replicating extrachromosomal vectors or vectors which integrate into a host genome. Generally, expression vectors include transcriptional and translational regulatory nucleic acid operably linked to the nucleic acid encoding the β-type DNA polymerase. "Operably linked" in this context means that the transcriptional and translational regulatory DNA is positioned relative to the coding sequence of the β-type DNA polymerase in such a manner that transcription is initiated. Generally, this will mean that the promoter and transcriptional initiation or start sequences are positioned 5' to the polymerase coding region. The transcriptional and translational regulatory nucleic acid will generally be appropriate to the host cell used to express the β-type DNA polymerase; for example, transcriptional and translational regulatory nucleic acid sequences from yeast will be used to express the β-type DNA polymerase in yeast. Numerous types of appropriate expression vectors, and suitable regulatory sequences are known in the art for a variety of host cells.

In general, the transcriptional and translational regulatory sequences may include, but are not limited to, promoter sequences, signal sequences, ribosomal binding sites, transcriptional start and stop sequences, translational start and stop sequences, termination and poly A signal sequences, and enhancer or activator sequences. In a preferred embodiment, the regulatory sequences include a promoter and transcriptional start and stop sequences.

Promoter sequences encode either constitutive or inducible promoters. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Repressible promoters, such as the methionine promoter, are also useful. Hybrid promoters, which combine elements of more than one promoter, are also known in the art, and are useful in the invention.

In addition, the expression vector may comprise additional elements. For example, the expression vector may have two replication systems, thus allowing it to be maintained in two organisms, for example in yeast for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used. For example, yeast selectable markers include ADE2, HIS3, LEU2, TRP1, URA3, LEU2, DFR and ALG7, which confers resistance to tunicamycin; the G418 resistance gene, which confers resistance to G418; and the CUP1 gene, which allows yeast to grow in the presence of copper ions. The β-type DNA polymerases of the invention are produced by culturing a host cell transformed with an expression vector containing nucleic acid encoding a β-type DNA polymerase, under the appropriate conditions to induce or cause expression of the β-type DNA polymerase. The conditions appropriate for β-type DNA polymerase expression will vary with the choice of the expression vector and the host cell, and will be easily ascertained by one skilled in the art. For example, the use of constitutive promoters in the expression vector will require optimizing the growth and proliferation of the host cell, while the use of an inducible or repressible promoter requires the appropriate growth conditions for induction or derepression.

In a preferred embodiment, the β-type DNA polymerase is purified or isolated after expression. The β-type DNA polymerases may be isolated or purified in a variety of ways known to those skilled in the art depending on what other components are in the sample. Standard purification methods include electrophoretic, molecular, immunological and chromatographic techniques, including ion exchange, hydrophobic, affinity, and reverse-phase HPLC chromatography, and chromatofocusing. For example, the HA/β-type DNA polymerase fusion protein may be purified using a standard antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the β-type DNA polymerase. In some instances no purification will be necessary.

Appropriate host cells include yeast, bacteria, archebacteria, fungi such as filamentous fungi, and plant and animal cells, including mammalian cells. Of particular interest are *Saccharomyces cerevisiae* and other yeasts, *E. coli*, *Bacillus subtilis*, *Pichia pastoris*, SF9 cells, C129 cells, 293 cells, Neurospora, and CHO, COS, HeLa cells, immortalized mammalian myeloid and lymphoid cell lines. A preferred host cell is yeast, and the most preferred host cell is *Saccharomyces cerevisiae*.

In a preferred embodiment, β-type DNA polymerase is produced in yeast cells. Yeast expression systems are well known in the art, and include expression vectors for *Saccharomyces cerevisiae*, *Candida albicans* and *C. maltosa*, *Hansenula polymorpha*, *Kluyveromyces fragilis* and *K. lactis*, *Pichia guillerimondii* and *P. pastoris*, *Schizosaccharomyces pombe*, and *Yarrowia lipolytica*. The methods of introducing exogenous nucleic acid into yeast hosts, as well as other hosts, is well known in the art, and will vary with the host cell used.

In a preferred embodiment, the Pichia expression system is used. For example, Invitrogen® sells a Pichia Expression Kit which may be used.

In a preferred embodiment, the β-type DNA polymerases of the invention are expressed in mammalian cells. Mammalian expression systems are also known in the art. A mammalian promoter is any DNA sequence capable of binding mammalian RNA polymerase and initiating the downstream (3') transcription of a coding sequence for β-type DNA polymerase into mRNA. A promoter will have a transcription initiating region, which is usually placed proximal to the 5' end of the coding sequence, and a TATA box, located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

Some genes may be expressed more efficiently when introns are present. Several cDNAs, however, have been efficiently expressed from vectors that lack splicing signals. Thus, in some embodiments, the nucleic acid encoding the β-type DNA polymerase includes introns.

The methods of introducing exogenous nucleic acid into mammalian hosts, as well as other hosts, is well known in the art, and will vary with the host cell used. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the ATCC, including but not limited to, Chinese hamster ovary (CHO) cells, HeLa cells, baby hamster kidney (BHK) cells, monkey kidney cells (COS), human hepatocellular carcinoma cells, and a number of other cell lines.

In a preferred embodiment, β-type DNA polymerases are expressed in bacterial systems. Bacterial expression systems are well known in the art.

A suitable bacterial promoter is any nucleic acid sequence capable of binding bacterial RNA polymerase and initiating the downstream (3') transcription of the coding sequence of β-type DNA polymerase into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E.coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the β-type DNA polymerase in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, β-type DNA polymerases are produced in insect cells. Expression vectors for the transformation of insect cells, and in particular, baculovirus-based expression vectors, are well known in the art. Briefly, baculovirus is a very large DNA virus which produces its polyhedrin coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the β-type DNA polymerase; a wild type baculovirus with a sequence homologous to the baculovirus-specific fragment in the transfer vector (this allows for the homologous recombination of the heterologous gene into the baculovirus genome); and appropriate insect host cells and growth media.

After inserting the nucleic acid encoding the β-type DNA polymerase into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form; for example the "MaxBac" kit from Invitrogen in San Diego.

Recombinant baculovirus expression vectors have been developed for infection into several insect cells. For example, recombinant baculoviruses have been developed for *Aedes aegypti, Autographa californica, Bombyx mori, Drosophila melangaster, Spodoptera frugiperda*, and *Trichoplusia ni*.

Once expressed, β-type DNA polymerases are used as nucleic acid polymerases. In general, the β-type DNA polymerases of the invention share many biochemical and enzymatic characteristics with the mammalian DNA polymerase βs. It is to be understood that the complete biological function and enzymatic activity of the β-type DNA polymerases may have additional uncharacterized enzymatic functions.

Accordingly, the β-type DNA polymerases of the invention are capable of nucleic acid synthesis, using a primed template. As used herein, "synthesis" in general means the addition of at least one nucleotide to a primed template. Synthesis may include replication, such as DNA replication, as well as a role in repair functions, such as in the addition of nucleotides after the excision of mismatches, which introduces gaps. For example, the repair of DNA by glycosylase of G/T mismatches results in a single nucleotide gap. It may also include synthesis of RNA, such as in the synthesis of catalytic RNA. It may also include reverse transcription, such as copying mRNA into cDNA.

In the preferred embodiment, a primed template is required for synthesis, and thus the β-type DNA polymerases of the invention do not possess substantial terminal transferase activity. However, the amino acid sequences of preferred embodiments contain sequences which are homologous to terminal transferase. In particular, preferred embodiments include at least about 32% amino acid homology over a 119 amino acid region of the 509 amino acid mouse terminal transferase protein.

In one embodiment, DNA is used as the template for synthesis. This DNA may be a synthetic DNA polymer or a naturally occurring DNA. Alternative embodiments utilize RNA as the template, thus conferring reverse transcriptase activity. In a preferred embodiment, this reverse transcriptase activity is observed in the presence of either Mg++ or Mn++. Alternative embodiments exhibit reverse transcriptase activity only in the presence of Mn++, in a manner similar to the mammalian DNA polymerase βs.

In one embodiment, the β-type DNA polymerases of the invention incorporate deoxyribonucleotides into the synthesis of nucleic acid. In an alternative embodiment, ribonucleotides are incorporated. In this embodiment, ribonucleotides are incorporated in the presence of either Mg++ and Mn++. In a further embodiment, both deoxyribo- and ribonucleotides are incorporated.

Other characteristics of the β-type DNA polymerases of the invention that are shared by the mammalian DNA β-polymerases include resistance to aphidicolin and sensitivity to dideoxynucleoside triphosphate substrates. However, the β-type DNA polymerases of the invention are not necessarily resistant to the general sulfhydryl blocker N-ethylmaleimide.

β-Type DNA polymerases, similar to mammalian DNA polymerase βs, exhibit loose substrate specificity, as evidenced by comparatively efficient incorporation of ddntps and even rNTPs, and extensive noncomplementary incorporation in the presence of a single dNTP (Rein 1990). The β-type DNA polymerase from yeast is the least discriminating of the known enzymes as evidenced by this loose substrate specificity in the presence of either Mg++ or Mn++. Accordingly, β-type DNA polymerases are useful in the synthesis of nucleic acids with modified or labelled nucleotides, as well as nucleic acids with base pair mismatches.

In this embodiment, the enzyme is contacted with a primed template in the presence of at least one activated nucleotide. In a preferred embodiment, at least one adenosine activated nucleotide, at least one cytidine activated nucleotide, at least one guanosine activated nucleotide, and at least one thymidine activated nucleotide are used, to keep the fidelity of the enzyme as high as possible. Alternatively, at least one adenosine activated nucleotide, at least one cytidine activated nucleotide, at least one guanosine activated nucleotide, and at least one uridine activated nucleotide are used. By the term "nucleotide" herein is meant either a nucleotide or a nucleoside. A nucleoside comprises a purine or pyrimidine base linked to a D-ribose or D-deoxyribose; nucleotides are a nucleoside containing at least one phosphate group. The purine or pyrimidine bases are most often adenine, guanine, cytosine, thymine and uracil, although additional embodiments may utilize other naturally occurring or synthetic purines and pyrimidines. An "activated nucleotide" is a nucleotide in a form which can be added, for example via a phosphodiester bond, by a β-type DNA polymerase to a primed template. Generally, an activated nucleotide will be a nucleoside triphosphate, i.e., a nucleoside "charged" with three phosphate groups, although alternative embodiments will utilize other functional groups which allow the addition of the activated nucleotide to a growing nucleic acid by a β-type DNA polymerase.

In a preferred embodiment, DNA is synthesized. In alternate embodiments, RNA is synthesized, or nucleic acid containing a mixture of deoxyribo- and ribonucleotides.

In the preferred embodiment, more than one nucleotide is added to the primer, and preferably at least about 10 to 20 nucleotides are added per binding event. That is, each time the enzyme binds to the primed template, multiple nucleotides are added to the primer; this is defined as processivity and is a characteristic which varies among the different classes of polymerases. Thus in the preferred embodiment, the β-type DNA polymerases of the invention are highly processive.

In alternative embodiments, β-type DNA polymerases are non-processive, synthesizing only short stretches of nucleic acid in a single binding event.

The additional ability of the β-type DNA polymerases to incorporate nucleotides into nucleic acid with imperfect fidelity forms the basis of the utility of the invention for use in DNA synthesis.

In one embodiment, a β-type DNA polymerase is used to synthesize nucleic acid which contains mutations, or base pair mismatches when compared to the template sequence. Thus the β-type DNA polymerases of the invention are useful in the generation of random, site-specific or region-specific nucleic acid mutations. In this embodiment, a β-type DNA polymerase is contacted or added to a primed template, in the presence of at least one activated nucleotide. The available pool of activated nucleotides is what drives the formation of mutations, or mismatches, in the formation of nucleic acid. Thus a β-type DNA polymerase will add an incorrect base if that incorrect base is preferentially available to the enzyme as compared to the correct one. For example, in the synthesis of DNA, if the available pool of nucleotides contains a single base, only two bases, or only three bases, mutations can result. In addition, if all four bases are in the pool, but the ratio varies significantly from 1:1:1:1, mutations can also result. The determination of experimental conditions for the creation of mutations, as well as the analysis of the resulting mutations, is easily and routinely done using techniques well known in the art.

The imperfect fidelity of the β-type DNA polymerases also enables the use of the enzyme to incorporate unconventional nucleotides into a nucleic acid. In a preferred embodiment, nucleic acid which contains at least one modified nucleotide is synthesized. By "modified nucleotide" herein is meant a non-naturally occurring nucleotide or nucleotides. For example, a modified nucleotide may contain a unique functional group; i.e., for the subsequent attachment of a label or other moiety to a precise location. For instance, the 2' position of the ribose of the deoxyribo- or ribonucleotide may be modified to contain an amino group using established chemical techniques. Alternatively, a modified nucleotide may contain a different bond type, length or orientation. For example, a modified nucleotide comprising two or more nucleotides linked together via a unique or atypical bond, for instance, a phosphoramide, phosphorothioate, phosphorodithioate, O-methyphosphoroamidite or peptide nucleic acid linkage. This may also enable the subsequent addition of labels or other functional groups. In a preferred embodiment, nucleotides are modified such that subsequent incorporation into a nucleic acid by a β-type DNA polymerase renders the nucleic acid resistant to degradation, i.e., by exo- or endo-nucleases. Thus, the β-type DNA polymerases of the invention allow the creation of nucleic acid, for example thiophosphate containing anti-sense nucleic acid, which is stable to in vivo or in vi tro degradation.

In the most preferred embodiment, nucleic acid which contains at least one labelled nucleotide is synthesized. By "labelled nucleotide" herein is meant a nucleotide which has at least one element, isotope or chemical compound attached, to enable the detection of the nucleotide. In general, labels fall into three classes: a) isotopic labels, which may be radioactive or heavy isotopes; b) immune labels, which may be antibodies or antigens; and c) colored or fluorescent dyes.

In this preferred embodiment, the β-type DNA polymerases are used in nucleic acid sequencing. Current standard techniques in the art utilize a DNA polymerase and radioactive dideoxynucleotides. Thus in one embodiment β-type DNA polymerases may be used as substitutes in these well known reactions. In addition, the use of radioisotopes is generally considered undesirable and thus methods utilizing non-radioactive labels are preferred. However, known polymerases generally accept bulky labelled nucleotides as substrates only inefficiently or not at all. Accordingly, the β-type DNA polymerase of the invention are useful in the synthesis or generation of nucleic acid containing at least one or more labelled nucleotides. The reactions utilizing labelled nucleotides as a substrate for β-type DNA polymerase will proceed as the reactions for non-labelled nucleotides, with routine adjustments in the time of the reaction, buffers and other reaction conditions to accommodate the labelled nucleotides.

The β-type DNA polymerases may be used to generate nucleic acid that contains one or more labels from one or more of the three types of labels. For example, one base may be labelled with one type of label, a second base may be labelled with a different type of label, and so on. Alternatively, the bases may all be labelled with a single type of label.

In one embodiment, the β-type DNA polymerases of the invention are variant or mutant β-type DNA polymerases. These variants fall into one or more of three classes: substitutional, insertional or deletional variants. These variants ordinarily are prepared by site specific mutagenesis of nucleotides in the DNA encoding the β-type DNA polymerase, using cassette mutagenesis or other techniques well known in the art, to produce DNA encoding the variant, and thereafter expressing the DNA in recombinant cell culture as outlined above. However, variant β-type DNA polymerase fragments having up to about 100–150 residues may be prepared by in vitro synthesis using established techniques. Amino acid sequence variants are characterized by the predetermined nature of the variation, a feature that sets them apart from naturally occurring allelic or interspecies variation of the β-type DNA polymerase amino acid sequence. The variants typically exhibit the same qualitative biological activity as the naturally occurring analogue, although variants are also selected to modify the characteristics of β-type DNA polymerase as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed β-type DNA polymerase variants screened for the optimal combination of desired activity. In some embodiments, random mutagenesis of the entire gene may be conducted. Techniques for making substitution mutations at predetermined sites in DNA having a known sequence are well known, for example, M13 primer mutagenesis. Screening of the mutants is done using established techniques for the assay of polymerase activities.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger. For example, an N-terminal deletion of about 200 amino acids of the yeast β-type DNA polymerase protein is possible. In addition, both N- and C-terminal deletions of the full length protein are useful.

Substitutions, deletions, insertions or any combination thereof may be used to arrive at a final derivative. Generally these changes are done on a few amino acids to minimize the alteration of the molecule. However, the epitope insertion in the β-type DNA polymerase described herein demonstrates that large alterations will be tolerated. For example, 11 amino acids can be inserted with complete retention of biological activity.

When small alterations in the characteristics of the β-type DNA polymerase are desired, substitutions are generally made in accordance with the following table:

TABLE I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table I. For example, substitutions may be made which more significantly effect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophobic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity as the naturally-occurring analogue, although variants also are selected to modify the characteristics of the polypeptide as needed. For example, epitope coding sequences may be added or protease recognition sites eliminated, without altering the biological activity of the polypeptide. The evaluation of the new characteristics of the polypeptide will vary with the alteration. For example, the addition of an epitope coding sequence may be evaluated by antibody binding studies, and the deletion of a protease recognition site evaluated by treatment with protease followed by gel electrophoresis or a biological activity assay. These guidelines allow one skilled in the art to successfully evaluate the effect and characteristics of any insertion, deletion or substitution of amino acid sequence in a β-type DNA polymerase.

Alternatively, the variant β-type DNA polymerase may be designed such that the biological activity of the protein is altered. For example, amino acids Arg183, Asp190 and Asp192 (rat notation) are conserved from yeast to man and are required for rat enzyme function (Date et al., Biochemistry 29, 5027–5034 (1990); Date et al., Biochemistry 30, 5286–5292 (1991)). Mutations in this region in the rat enzyme alter the $K_m$ for primer termini suggesting that these residues participate in primer recognition, and thus are candidate residues for the generation of variants in the yeast enzyme. In the rat DNA polymerase β, Ser55 and Ser44 are sites for protein kinase C phosphorylation (Tokui et al., J. Biol. Chem. 266, 10820–10824,(1991)). Phosphorylation at the Ser55 site inactivates the enzyme. The Ser55 corresponding site in the yeast β-type DNA polymerase, Ser230, is thus a candidate for variant analysis. The Ser44 site is a Gln in the yeast β-type DNA polymerase, and is also thus a candidate for variant analysis.

As a subclass of deletion mutants, β-type DNA polymerase with N- or C-terminal truncations, or fragments of β-type DNA polymerase, are included within the definition of a β-type DNA polymerase enzyme. In this regard, N- or C-terminal truncations, or both, may be made which retain full or partial enzymatic activity. For example, the N-terminus of the yeast β-type DNA polymerase is probably not involved in the DNA polymerase activity of the enzyme, and thus may be deleted using standard techniques. This is evidenced by the homology of yeast β-type DNA polymerase to rat DNA polymerase-β is in the C-terminal portion of the β-type DNA polymerase, and that there is an approximately 190 amino acid extension in the N-terminal region of the β-type DNA polymerase from yeast. In addition, an 11 amino acid extension, in the form of the hemagglutinin epitope, may be added to the N-terminus without a significant loss of enzyme activity.

Therefore, in a preferred embodiment, a β-type DNA polymerase contains about 580 amino acids, in contrast to the 393 amino acids of the mammalian DNA polymerase βs. However, β-type DNA polymerases which are missing some or all of the N-terminal addition or extension, comprising 190 amino acids in the yeast β-type DNA polymerase, are included within the definition of β-type DNA polymerase if the requisite homology is present. Accordingly, β-type DNA polymerases which are less than 400 amino acids long but exhibit at least about 50% homology with the sequence depicted in FIG. 5 (SEQ ID NO:2) are included within the scope of the invention.

Alternatively, N- or C-terminal truncations, or both, may decrease or eliminate the enzymatic activity of the enzyme. However, variant β-type DNA polymerases which display low or negligible biological activity are included in the definition of β-type DNA polymerase if the variant exhibits at least 50% homology with full-length β-type DNA polymerase and shares at least one immunological epitope in common with the full-length β-type DNA polymerase.

β-Type DNA polymerase derivatives or fragments or variants that are not enzymatically active but which are capable of cross-reacting with antisera or antibodies to enzymatically active β-type DNA polymerase are useful in several applications. These derivatives are useful as reagents in diagnostic assays for β-type DNA polymerase or antibodies to β-type DNA polymerase, or when insolubilized in accord with known methods as agents for the purification of β-type DNA polymerase antibodies from antisera or hybridoma culture supernatants. These derivatives are also useful as immunogens to enzymatically active β-type DNA polymerase. In addition, these derivatives are useful in assays of polymerase functions, such as assays of binding interactions among the polymerases and transcription factors, and the role of β-type DNA polymerases in cellular functioning.

In additional embodiments, the β-type DNA polymerases of the invention are incorporated into kits for nucleic acid synthesis. In one embodiment, the kit comprises a container or receptacle with a single aliquot of a β-type DNA polymerase. A single aliquot will be determined on the basis of the specific activity of the particular β-type DNA polymerase used, and is similar to the amount of known DNA polymerases used in such reactions. In alternative embodiments, the kit comprises multiple aliquots of a β-type DNA polymerase. Other compounds may also be included in the kit. For example, one or more types of activated nucleotides may be included. For instance, the kit may some or all of the triphosphates or dideoxy-triphosphates of adenine, cytosine, guanine, thymidine or uracil, or other naturally occurring or synthetic nucleotides. Some or all of the activated nucleotides may be modified or labelled, for example with radioisotopes, antibodies or dyes, as outlined above.

The kit may have additional packaging or compounds such as tubes, beakers, holders, pipettes, buffers, salts, acids or bases. The kit may also include materials for polyacrylamide or agarose gels, as well as materials for detecting the label used. In some embodiments, the kit contains primers, templates or both.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

In Vitro Mutagenesis of the Yeast β-type DNA Polymerase

In order to distinguish the β-type DNA polymerase from other known cellular polymerases, the β-type DNA polymerase from S. cerevisiae was tagged with the influenza hemagglutinin epitope MYPYDVPDYASL (SEQ ID NO:3), plus an additional GGP (Field et al., Mol. Cell. Biol. 8 2159–2165 (1988)) to the $NH_2$ terminus of the protein. The fusion protein is referred to as HA ypolβ.

In addition, since β-type DNA polymerases have never been detected in extracts of vegetatively growing cells, and thus putatively expressed at low levels from its native promoter, the fusion protein was placed under control of the inducible GAL1,10 promoter.

pYCR14C, a Bluescript derived-plasmid (Stratagene) containing the open reading frame YCR14C, identified by Bork et al., Nature 358, 287 (1992) as a putative DNA polymerase, was obtained from Bénédicte Purnell at the Universite Catholique de Louvain. This plasmid contains DNA coding for the yeast β-type DNA polymerase.

The fusion containing the hemagglutinin epitope fused to the N-terminus of the YCF14C open reading frame was constructed employing site-directed mutagenesis using the technique of Taylor et al., Nucleic Acid Res. 13:8765–8785 (1985), and oligol:

oligol: 5' TTTACCCTTTAGAGAAGGACCAC-CCAAGCTAGCGTA GTCTGGGACGTCG-TATGGGTACATGAATTCATTGTCT AACAGGTC 3' (SEQ ID NO:4)

The fusion was confirmed by DNA sequencing using standard techniques and inserted into the EcoR1 site of pSEY18 GAL to form pGAL18HAβ. pSEY18 GAL is a plasmid which has the GAL1 and GAL10 promoters in a URA3, 2 μm plasmid. An EcoR1 site is positioned at the N-terminus of the protein.

The resulting pGAL18HAβ mplasmid was transformed into the BJ5459 strain, obtained from Yeast Genetic Stock Center as shown in Table 1, using well known techniques.

TABLE 1

Yeast Strains

| Strain | Genotype | Source[a] |
|---|---|---|
| 6210 | α leu2-3,112, ura3-52 his3-Δ200 trpl-Δ901 lys2-01 suc2-Δ9 | S. Emr |
| 6211 | a leu2-3,112, ura3-52 his3-Δ200 trpl-Δ901 ade2-101 lys2 | S. Emr |
| 6210β-2A | a leu2-3,112, ura3-52 his3-Δ200 trpl-Δ901 | |
| 6210β-4A | a leu2-3,112, ura3-52 his3-Δ200 trpl-Δ901 ade2-101 suc2-Δ9 | |
| 6210β-2C | α (pol4Δ:URA3) ura3-52 leu2-3,112 his3-Δ200 trpl-Δ901 ade2-101 suc2-Δ9 | |
| 6210β-2D | α (pol4Δ:URA3) ura3-52 leu2-3,112 his3-Δ200 trpl-Δ901 ade2-1101 | |
| 6210β-10C | a (pol4Δ:URA3) ura3-52 leu2-3,112 his3-Δ200 trpl-Δ901 suc2-Δ9 | |
| D6212 | 6210 × 6211; POL+/POL+ | |
| D6213 | 6210β-2C × 6210β-10C; pol4Δ/pol4Δ | |
| D6214 | 6210β-2D × 6210β-10C; pol4Δ/pol4Δ | |
| g388-1B | a leu2 his1-1 trp2 can1 qal2 | M. Hoekstra; J. Game |
| g388-2D | a hom3-10 his1-7 ade2 | M. Hoekstra; J. Game |
| g857 | g388-1B × g388-2D | |
| BJ5459 | a ura3-52 trpl lys2-801 leu2Δ1 his3Δ200 pep4:HIS3 | Yeast Genetic Stock Center |
| X12-68 | a rad1-1 ade2-1 gal2 | Yeast Genetic Stock Center |
| M754-6D | a rad54-3 tup7-1 his1-1 trp2-1 ade4 leu2-1 | |

[a]Unless otherwise noted, strains were constructed in laboratory.

Example 2

Expression and Immunoprecipitation of Yeast β-type DNA Polymerase

BJ5459 cells containing the pGAL18HAβ plasmid were grown in 2% raffinose synthetic media to $10^7$ cells/ml; galactose was added to 2%, and cells were harvested 6 hours later, and frozen at −70° C. Cells were lysed in buffer containing 0.05 M tris pH 8.0, 0.05 M NaCl, 10% glycerol, 1 mM EDTA, 1 mM DTT in liquid $N_2$ by grinding with a mortar and pestle. The powder was thawed, and protease inhibitors, (1 mM PMSF, 2 mM benzamidine, 2 μg/ml pepstatin A, 1 μg/ml leupeptin) were added. Cells were centrifuged at 30,000 rpm in a Ti 50 rotor for 20 min and 200 µg of protein was used in each immunoprecipitation. Yeast extract was mixed with 30 µg of 12CA5 monoclonal antibody for 2 hours at 0° C. 12CA5 is a subclone of H26D08-mouse IgG-2b which was raised against the influenza hemagglutinin peptide (75–110) (Field et al., 1988). 30 µl of 10% protein A beads was added for 1.5 hours, beads were washed five times with TBS+0.1% Tween, 2 times with 2×assay buffer, and resuspended in 30 µl of 2×assay buffer. 30 µl of [$^3$H]NTP, DNA, $Mg^{++}$ or $Mn^{++}$ was added to start the reaction. 10 to 50 µg of peptide HA1 were used as competitor.

Immunoprecipitates were separated by SDS-PAGE, transferred to nitrocellulose and probed with the hemagglutinin epitope-specific antibody, 12CA5. A 75 kDa band appeared in the lane with protein from pGAL18HAβ extracts but not in the lane with protein from the pSEY18GAL vector extracts (data not shown).

In each set of assays to measure the DNA polymerase activity of the immunoprecipitates, controls included immunoprecipitation in the presence of molar excess of the HA peptide, immunoprecipitation of extracts from cells transformed with the pSEY18GAL vector (no insert), and sometimes immunoprecipitations in the presence of protein A beads but not 12CA5 antibody. Since DNase I treated DNA ("activated" and gapped DNA) has been reported to be a preferred substrate for DNA polymerase βs, initial assays were performed with this substrate.

All assays were carried out at 37° C. for 1 hour. DNA polymerase assay mixtures contained 1× assay buffer (50 mM Tris pH 8.0, 10 mM $MgCl_2$, 50 mM NaCi, 0.5 mg/ml BSA) and 100 µM each dATP, dGTP, dCTP, [$^3$H]dTTP (300 cpm/pmol). The DNA concentration was 100 4µ/ml activated DNA or 100 µg/ml poly dA-oligo dT (20:1). $MnCl_2$ was substituted at 1 mM for $MgCl_2$. Assays using rA-dT as a primer-template were carried out at a concentration of 250 µg/ml. The rA-dT ratio was 20:1.There were approximately 16,000 pmoles dA and 60 pmol of primer termini in the dA-dT (20:1) reaction and 40,000 pmol rA and 150 pmol of primer termini in the rA-dT reaction. Assays in the presence of 30 µg/ml aphidicolin were in the presence of 10 µM dCTP. Assays measuring incorporation rUTP were carried out at a concentration of 100 µM rUTP. Assays measuring sensitivity to dideoxythymidine triphosphate were carried out in the presence of 10 µM dTTP. After incubation, assay mixtures were spotted on DE81 filters, washed 6 times in 0.5M $Na_2PO_4$, washed once with $H_2O$, once with ethanol and counted in toluene based scintillation fluor.

The results, shown in Table 2,indicate that DNA polymerase activity was immunoprecipitated by 12CA5 antibody in galactose induced cultures containing the plasmid pGALHAβ. The activity was 10-fold higher than in controls. This results demonstrates that the product of ORF YRC14C has DNA polymerase activity and is the fourth nuclear DNA polymerase in S. cerevisiae, and is designated β-type DNA polymerase; the yeast gene is designated POL4.

Data from Table 2 also shows that yeast β-type DNA polymerase is inhibited by ddTTP, which does not inhibit DNA polymerase α, δ and ε at the levels used here. The new polymerase is sensitive to the general sulfhydryl blocker N-ethylmaleimide (10 mM), in contrast to rat DNA polymerase β (Stalker et al.,Biochemistry 15:3114–3121 (1976); Yoshida et al., Supra). In addition, the yeast β-type DNA polymerase is resistant to aphidicolin at a concentration of 30 µg/ml, which completely inhibits DNA polymerases α, δ and ε. This suggests that an active site that is structurally more flexible as evidenced by broad spectrum substrate acceptance can accommodate aphidicolin, whereas the drug significantly interferes with enzymes with more stringent recognition determinants. If this were true, then one would expect that mutations that relax the substrate specificity of DNA polymerase α might also decrease aphidicolin sensitivity. Mutations that increase misinsertion frequency by DNA polymerase α have recently been identified and, as predicted, they do increase aphidicolin resistance (Copeland et al., J. Biol. Chem. 268, 11041–11049 (1993); Copeland et al., J. Biol. Chem, 268 11028–11040 (1993)).

Additional characteristics that readily distinguish DNA polymerases and suggest in vivo roles are primer-template requirement, substrate specificity and associated activities, such as nuclease. The yeast β-type DNA polymerase shows significant activity with $dA_{500} \cdot T_{12-18}$, 20:1,and thus, like mammalian polβ, uses synthetic homopolymers as primer-templates as well as DNA (Tables 2 and 3). The results allow an 5 estimation of the processivity of the yeast β-type DNA polymerase. In a reaction containing dA-dT as primer-template, with 16,000 pmol template and 60 pmol of primer termini, 480 pmol of dTTP are incorporated. Thus, the primer termini are utilized more than once in the reaction; but, as for mammalian DNA polymerase β, processivity is low.

In the case of the reverse transcription reaction of Table 3,the incorporation of dTTP was not significantly greater than the number of primer termini in each reaction and usually much less. This suggests that yeast β-type DNA polymerase adds one nucleotide in these reactions and dissociates. However, the inefficiency could be due to having suboptimal assay conditions and the activity may have physiological significance. For example, one cellular role of reverse transcriptase is processing of telomeres. A yeast telomerase has not been definitively identified, and, therefore, the possibility that yeast β-type DNA polymerase participates in telomere synthesis deserves further investigation. The only yeast DNA polymerase directly implicated in de novo telomere synthesis is DNA polymerase a, since temperature sensitive mutants synthesize extra long telomeres, perhaps due to a faulty interaction with telomerase (see Campbell and Newlon, 1991).

Most DNA polymerases are incapable of initiating synthesis de novo, i.e., they require a primer. During replication the primer is usually provided by a primase; during repair the primer is provided by a nick. To test for a primer requirement, synthesis on the poly dA template alone was measured. No synthesis was observed, indicating that the enzyme doesn't initiate de novo (Table 3). The absence of synthesis also indicates that yeast β-type DNA polymerase is incapable of a nontemplated polymerase reaction primed by the 3' OH terminus of the poly dA. Thus, neither yeast β-type DNA polymerase, rat nor human DNA polymerase βs have terminal transferase activity, although DNA polymerase βs are homologous to terminal transferase (Anderson et al., supra; Matsukage et al., J. Biol. Chem. 262, 8960–8962 (1987)).

Many DNA polymerases can, under the right conditions, copy RNA as well as DNA templates. Mammalian DNA polymerase β was, in fact, first discovered in a search for cellular reverse transcriptases. Thus, it is interesting that yeast β-type DNA polymerase has significant reverse transcriptase activity. The yeast activity is observed in the presence of either Mg$^{++}$ or Mn$^{++}$, whereas the rat polβ reverse transcriptase activity has been described only in the presence of Mn$^{++}$ (Wang, supra; Ono et al., supra; Yoshida et al., supra).

Not only can ypolβ utilize polyribonucleotides as templates, it can also use ribonucleoside triphosphates as substrates, as evidenced by the ability to incorporate rUTP on dA-dT and rA-dT in the presence of either Mg$^{++}$ or Mn$^{++}$. Other DNA polymerases, such as E. coli DNA polymerase I, also incorporate ribonucleotides. However, the reaction is only efficient in the presence of Mn$^{++}$, which is known to reduce the ability of DNA polymerases to discriminate between correct and incorrect nucleotide substrates. Mammalian DNA polymerase β also shows markedly reduced ability to discriminate among substrates compared to α-type polymerases, since in copying DNA it has 20–50% as much activity in the presence of a single dNTP as in the presence of all four dNTPs (Rein et al., supra). Thus, yeast β-type DNA polymerase appears to exhibit a wider range of substrate specificity in the presence of Mg$^{++}$ than any known DNA polymerase. Despite the ability to incorporate rUTP, polymerization of dTTP with dA-dT as the primer template is the preferred reaction of yeast β-type DNA polymerase suggesting that it functions as a DNA polymerase rather than as an RNA polymerase in vivo. (As shown by the control experiments in Table 3, the polymerase activities are specific for the HA polβ fusion protein).

Most DNA polymerases have associated activities such as pyrophosphorolysis, pyrophosphate exchange or exonuclease. Mammalian DNA polymerase β, however, lacks such activities. Since yeast β-type DNA polymerase has a 30 KDa NH$_2$-terminal region not in the mammalian enzyme, it was important to assess additional activities. Yeast β-type DNA polymerase, like mammalian polβ, showed no 3' exonuclease activity on a substrate prepared by labeling poly dT at the 3'-end with terminal transferase (data not shown).

TABLE 2

DNA Polymerase β Activity in 12CA5 Immunoprecipitates

| Primer-template | Condition | Polβ Activity[1] (1) | Polβ Activity[1] (2) |
|---|---|---|---|
| DNA | Complete[2] | 101 | 96 |
| DNA | Vector[3] | 13 | 12 |
| DNA | HA peptide[4] | 15 | 10 |
| DNA | No antibody | 9 | — |
| DNA | dCTP (10 mM) | 212 | 106 |
| DNA | Aphidicolin (30 mg/ml) | 162 | 78 |
| DNA | NEM (10 mM) | 8 | — |
| dA-dT (20:1) | Complete | 293 | 411 |
| dA-dT (20:1) | dTTP (10 mM) | 95 | 102 |
| dA-dT (20:1) | dTTP (10 mM)/ddTTP (10 mM) | 11 | 6 |
| dA-dT (10:1) | Complete | 105 | 244 |
| dA-dT (20:1) | Vector[2] | 11.8 | 16 |
| dA-dT (10:1) | Vector[2] | 10.5 | — |
| dA | Complete | — | 0.9 |

[1]The results of two separate experiments are reported. Activity represents extent of synthesis in 30 minutes.
[2]See examples for a complete description of the immunoprecipitation assay.
[3]Extracts were prepared from cells containing the pSEY18GAL vector alone.
[4]HA peptide was preincubated with the antibody before addition of antibody to the extracts as a specific competitor of precipitation.

TABLE 3 rNTP Incorporation and Reverse Transcriptase Activities of DNA Polymerase β

| Primer-template | [3]HNTP | Mg/Mn | HA polβ | +peptide | Vector alone | No Antibody |
|---|---|---|---|---|---|---|
| Experiment 1[2] | | | | | | |
| dA-dT | T | Mg | 480 | 64 | 16 | ND |
| dA-dT | T | Mn | 769 | ND | 7.2 | ND |
| dA-dT | U | Mg | 110 | 11 | 5.1 | 2.2 |
| dA-dT | U | Mn | 202 | 23 | 7.0 | 6.2 |
| rA-dT | T | Mg | 65 | 8.3 | 7.6 | 6.6 |
| rA-dT | T | Mn | 191 | 20 | 3.5 | 0.8 |
| Experiment 2[2] | | | | | | |
| dA-dT | U | Mg | 187 | 5.4 | 0.8 | 1.3 |
| dA-dT | U | Mn | 209 | 23 | 2.7 | 3.8 |
| rA-dT | T | Mg | 81 | 4 | 1.6 | 1.0 |
| rA-dT | T | Mn | 59 | 5.9 | 5.7 | 2 |
| rA-dT | U | Mg | 32 | 2.1 | 10.9 | 0.6 |
| rA-dT | U | Mn | 55 | 6.3 | 1.8 | 1.6 |

[1]Immunoprecipitations were performed and assays carried out as described in the Examples. HA polβ refers to the complete assay in extracts of strains carrying the tagged POL4 gene. +peptide indicates that the antibody used in the immunoprecipitation was incubated with the HA peptide competitor before addition to the extract. Vector alone indicates that immunoprecipitation was carried out on extracts of strains lacking the tagged POL4 gene. No Antibody means that antibody was omitted from the immunoprecipitation.
[2]The data are reported in separate experiments because they were carried out using immunoprecipitates prepared on different days. All assay reactions were carried out in duplicate.

Example 3

Creation of a Gene Disruption in Yeast β-type DNA Polymerase Gene

The following oligonucleotides were used in the generation of the deletion mutant:

oligo 2 (SEQ ID NO:5) 5' GGTGTCACTGACAA-GATCTCCCATGTCTCTAC TGGTGGTGCT-TCTTTGGTAGCAGCACGCCATA GTGACTGACG 3' oligo 3 (SEQ ID NO:6) GTAATAAGTAAAGGATAAA-CATGCGACCTGTT AGACAAATCGCACTCAT-GTTTGACAGCTTATCATC oligo 4 (SEQ ID NO:7) GAATTCTATCTCCGTAATCG-GTCTCGGTC oligo 5 (SEQ ID NO:8) AATAGCTTGGCAGCAA-CAGGG oligo 6 (SEQ ID NO:(9) GAATTCCCATGTCTC-TACTGGTGGTGGTGC The yeast β-type DNA polymerase gene was disrupted using a novel PCR procedure suggested by Dr. Shane Weber (Eastman Kodak Co., Rochester, N.Y.) through Chris Byrd (California Institute Of Technology). Oligo2 (SEQ ID NO:5) contains 45 bp of the DNA sequence of the yeast β-type DNA polymerase gene (the gene has been designated POL4) upstream of the ATG start and 20 bp of the tetracycline gene upstream of the HindIII site in YEP24. Oligo4 (SEQ ID NO:7) has 45 bp of DNA sequence 280 bp downstream of the TAA stop codon of the yeast 5-type DNA polymerase gene and 20 bp of the tetracycline gene 300 bp downstream from the HindIII site. These oligos were used as primers in a PCR reaction using YEp24 as a template. The URA3 gene is cloned into the tetracycline gene of pBR322 at the HindIII site in YEp24, and thus the PCR product is 1.5 kb and has an "insertion" of URA3 flanked by POL4 sequences. The PCR product was used directly to transform the ura3–52 diploid D6212 and Ura⁺ clones were selected. The oligonucleotides homologous to POL4 direct integration at the β-type DNA polymerase locus and the site of integration is marked by the URA3 gene in the PCR product.

The 45 bp of POL4 sequence polβ identity at the end of the PCR product is sufficient to direct the DNA to the POL4 locus in a small percentage of the transformants. Potential deletions were first checked in a PCR reaction using oligo5 (SEQ ID NO:8) and oligo4(SEQ ID NO:7). Oligo5 (SEQ ID NO:8) is 270 bp downstream from the HindIII site of the URA3 gene and oligo4 (SEQ ID NO:7) is 120 bp upstream of the ATG in the POL4 gene. An expected 450 bp fragment was observed in the transformant D6212-6. A Southern blot was done with the diploid using the URA3 gene as a probe and an expected 3.7 kb product was observed in the Dra I digest and an expected 3000 kb band was observed in a Cla I digest. The transformant was dissected and 4 viable segregants were observed. Southern blots were carried out on URA3 and ura3–52 segregants using a probe containing the yeast β-type DNA polymerase coding sequence. Expected DraI bands of 1110 and 2840 bp, HindIII bands of 700 and 400 bp, and an Xba-EcoRI band of 2580 bp were observed in the ura3–52 undisrupted segregant, but not in 2 URA3 segregants. Thus the entire coding region of POL4 was deleted from the chromosome.

Example 4

The Role of Yeast β-type DNA Polymerase in DNA Repair and Sporulation

Since DNA polymerase β is believed to be involved in DNA repair (Mosbaugh, et al., supra; Randahl et al., supra; Wiebauer et al., supra; Dianov et al., supra), UV and X-ray survival curves were carried out with pol4Δ strains.

The UV source was a Sylvania G15T8 germicidal lamp. The dosimetry was determined by ultraviolet meter Model #J-225 manufactured by Ultraviolet Products, San Gabriel, Calif. The X-ray source was a Pantak H-F 160 machine operated at 70 kV and 20 mamp. The cells were irradiated at 7 krads/min and 4.5 cm from the beam. The dosimetry was determined by the method of (Fricke and Morse, Am. J. Roentgenology 18: 426–430 (1927); Fregene, Radiation Res. 31, 256–272 (1967). Cells were harvested, washed in 10 mM Na PO₄, pH 6.8, irradiated in 10 mM Na PO₄, pH 6.8, diluted in the same buffer, plated and counted three days later.

As illustrated in FIG. 1, pol4Δ mutants are no more sensitive to UV than a related POL4+strain. A rad1-1 strain, X12-6B (Yeast Genetic Stock Center) was UV-irradiated as a control. The survival curve shows that yeast β-type DNA polymerase does not play an essential role in repair of UV-induced damage.

Since pol4Δ strains were not sensitive to UV, sensitivity to X-rays was investigated. Diploid strains were irradiated instead of haploid strains, as they are more resistant to irradiation and their survival curve is not biphasic. FIG. 2 illustrates an X-ray survival curve of four strains, a POL4Δ diploid, D6212,two pol4Δ diploid strains, and a rad54-3 haploid strain. rad54-3 strains are temperature sensitive for double strand break repair, and their haploid and diploid survival curves are the same. There is no significant difference in survival between POL4⁺ and pol4Δ strains, even at the highest dose, 30 krads (300 Gray), which probably induces 20 double strand breaks per diploid genome (Budd, unpublished). If one to two unrepaired double strand breaks are lethal in a diploid, then the survival curve suggests pol4Δ strains are completely proficient in double strand break repair.

The genotype of the strain used in the repair studies allowed the investigation of whether yeast β-type DNA polymerase was required for chromosome stability after irradiation. Strains D6212, D6213 and D6214 were heterozygous for ade2. The appearance of red colonies showed the sum of recombination and chromosome loss. rad52 strains lost chromosomes at a high frequency after irradiation (Mortimer et al., Proc. Natl. Acad. Sci. 78: 5778–5782 (1981)). The frequency of red colonies in both POL4⁺/POL4⁺ and pol4Δ/pol4Δ strains after 6 krads of irradiation was about 1%.

Thus, a high frequency of chromosome loss and recombination was not observed in pol4Δ diploid strains, suggesting that yeast β-type DNA polymerase does not play a major role in segregating chromosomes after irradiation. In conclusion, yeast β-type DNA polymerase is not essential for repair of either UV or X-ray induced damage.

The inability to demonstrate any essential role in mitotic replication or repair, and the high message levels of DNA polymerase β observed in rat testes prompted an investigation of the meiotic role of yeast β-type DNA polymerase. Diploid homozygous pol4Δ/pol4Δ strains were constructed, D6213 and D6214. Cells were grown in potassium acetate pre-sporulation medium overnight and then transferred to sporulation medium (1% potassium acetate). After two days spores were visible in a POL4/POL4 strain, D6212,and in a pol4Δ//pol4Δ/strain, D6213.After 3 days, about 30% of the D6212 cells, 20% of the D6213 cells, and about 0.1% of the D6214 cells had sporulated. The D6212 asci were primarily four spore tetrads. The D6213 asci were a mixture of four, three, and two spore tetrads with about twice as many three spore as four spore tetrads. The one ascus observed in the D6214 culture was a four spore tetrad. The meiotic products from the D6212 culture and D6213 culture were dissected. The spore viability in the D6212 culture was 100% and the spore viability of the D6213 culture was 90% (10 tetrads dissected). These observations suggest that yeast β-type DNA polymerase is not essential for either meiotic DNA replication or sporulation, nor any event required to produce viable spores. However, yeast β-type DNA polymerase is probably involved in meiosis, since two strains with deletions of the gene sporulated less efficiently than those without.

Example 5

Meiotic Expression Experiments

Since yeast β-type DNA polymerase is necessary for efficient sporulation, and since a comprehensive analysis of the RNA species transcribed from S. cerevisiae chromosome III during mitosis did not reveal an RNA at the POL4 locus (Yoshikawa and Isono, Yeast 6: 383–401 (1990)), the possibility that POL4 is induced in meiosis was tested.

RNA from cells at different stages in meiosis was purified from g357. Strain g857 is heteroallelic at H1S1, his1-1/his1-7,and is derived from the SK-1 background that sporulates in 12 hours and is used for high synchrony sporulation experiments. g357 was grown 12 hours in YKA medium: 1% potassium acetate, 1% peptone, 0.5% yeast extract, 0.5% (NH₄)₂SO₄, 0.017% YNB without amino acids and (NH₄)₂SO₄, 10 gm potassium acid phthalate pH 5.8 as described previously (Budd et al., 1989). Cells were resuspended in 1% potassium acetate and 5 mg/l, histidine, and samples were taken every 2 hours and analyzed for POL4 RNA and commitment to recombination. Cells sporulated after 10 h and sporulation was complete after 12 h. RNA was isolated by standard procedures. RNA formaldehyde gels were run and blotted onto Gene Screen, and washing and probing was carried out according to manufacturer's directions. The probe extended from 27 bp 5' to the ATG of POL4 to 200 bp 3' to the TAA. For assessing commitment to recombination, cells were plated on histidine-deficient complete medium in a classical interrupted meiosis protocol as previously described (Budd et al., 1989). The background frequency of His+ recombinants at 0 time is about $10^5$. The numbers given in FIG. 3 are the determined values normalized to the 0 time point.

As shown by the data in FIG. 3, a low abundance 2.2 kb POL4 message is observed in the mitotic culture and is induced about five fold two hours after initiating meiosis by resuspending the cells in potassium acetate media. The message level increases to about 30 fold more than in mitosis and persists to the end of meiosis at 10 hours. After 10 hours, asci can be observed in the culture but the message level remains high. To assess the progress through meiosis, we used an interrupted meiosis experiment, which establishes the time of commitment to recombination in the cells during the course of meiosis (Budd et al., 1989). At 2 hours, the number of HIS+ recombinants is the same as 0 hours. At 4 hours, there is a 10-fold increase in HIS+ recombinants.

The appearance of POL4 message before the increase in commitment to recombination is consistent with an involvement at any stage of DNA replication or recombination, but does not constitute evidence for a role in either. All lanes also show bands at 3.2 kb and 1.8 kb, but since these sizes correspond to ribosomal RNAs, they may be not be specific for POL4. In summary, a 2.2 kb MRNA having the expected size of the message of a 1749 bp ORF is expressed at low levels in vegetatively growing cells and is elevated during meiosis.

Inspection of the POL4 promoter reveals some elements, such as a T4C site, found in the IME1-dependent UAS known to regulate genes that are repressed in mitosis and expressed exclusively in meiosis, such as HOP1, RED1, SPO11 or SP013 (Vershon et al., 1992; Bowdish and Mitchell, 1993). The sequences diverge considerably, however, and their spacing and organization relative to the ATG are different, making their contribution to the regulation of POL4 somewhat questionable.

What is claimed is:

1. A recombinant, enzymatically active β-type DNA polymerase which is encoded by a nucleic acid which will hybridize under high stringency conditions to the nucleic acid shown in FIG. 4 (SEQ ID. NO:1), wherein said β-type DNA polymerase has reverse transcriptase activity in the presence of Mg$^{++}$.

2. A recombinant, enzymatically active β-type DNA polymerase which has the amino acid sequence shown in FIG. 5 (SEQ ID. NO:2).

3. An isolated nucleic acid encoding an enzymatically active β-type DNA polymerase which has the amino acid sequence shown in FIG. 5 (SEQ ID. NO:2).

4. An isolated nucleic acid which will hybridize under high stringency conditions to the nucleic acid shown in FIG. 4 (SEQ ID. NO:1), and which encodes an enzymatically active β-type DNA polymerase, wherein said β-type DNA polymerase has reverse transcriptase activity in the presence of Mg$^{++}$.

5. The isolated nucleic acid according to claim 4, which consists of the nucleic acid sequence shown in FIG. 4 (SEQ ID NO:1).

6. An expression vector comprising transcriptional and translational regulatory nucleic acid operably linked to the isolated nucleic acid according to claim 3, 4 or 5.

7. A host cell transformed with an expression vector according to claim 6.

8. A host cell containing the isolated nucleic acid according to claim 3, 4 or 5.

9. A method of producing a β-type DNA polymerase comprising:

a) culturing the host cell according to claim 8; and b) causing expression of said nucleic acid to produce said β-type DNA polymerase.

10. A kit for synthesizing nucleic acid comprising the recombinant β-type DNA polymerase according to claim 1.

11. A kit according to claim 10 further comprising at least one activated modified nucleotide.

12. A kit according to claim 11 wherein said modified nucleotide is a labeled activated nucleotide.

13. The β-type DNA polymerase according to claim 1 or 2, wherein said β-type DNA polymerase is resistant to about 30 μg/mL aphidicolin.

14. The isolated nucleic acid according to claim 3, 4, or 5, wherein said β-type DNA polymerase is resistant to about 30 μg/mL aphidicolin.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1756 base pairs
      (B) TYPE: nucleic acid
      (C) STRANDEDNESS: double
      (D) TOPOLOGY: both (ix) FEATURE:
      (A) NAME/KEY: CDS
      (B) LOCATION: 1..1746

(xi) SEQUENCE DESCRIPTION: SEQ ID NO:1:

```
ATG TCT CTA AAG GGT AAA TTT TTC GCC TTT TTA CCT AAT CCT AAC ACA        48
Met Ser Leu Lys Gly Lys Phe Phe Ala Phe Leu Pro Asn Pro Asn Thr
 1               5                  10                  15

TCT TCC AAT AAG TTC TTT AAG AGT ATA TTG GAG AAA AAG GGC GCC ACA        96
Ser Ser Asn Lys Phe Phe Lys Ser Ile Leu Glu Lys Lys Gly Ala Thr
                20                  25                  30

ATT GTG TCA AGT ATT CAA AAT TGT CTT CAA TCT AGC CGT AAG GAA GTT       144
Ile Val Ser Ser Ile Gln Asn Cys Leu Gln Ser Ser Arg Lys Glu Val
            35                  40                  45

ATC ATT TTG ATT GAG GAC TCC TTT GTT GAT TCT GAT ATG CAT TTG ACT       192
Ile Ile Leu Ile Glu Asp Ser Phe Val Asp Ser Asp Met His Leu Thr
 50                  55                  60

CAG AAA GAT ATT TTC CAA AGG GAA GCA GGC TTA AAT GAT GTC GAT GAA       240
Gln Lys Asp Ile Phe Gln Arg Glu Ala Gly Leu Asn Asp Val Asp Glu
 65                  70                  75                  80

TTT CTT GGT AAG ATT GAA CAG TCA GGC ATT CAA TGT GTG AAA ACC AGT       288
Phe Leu Gly Lys Ile Glu Gln Ser Gly Ile Gln Cys Val Lys Thr Ser
                85                  90                  95
```

```
TGC ATC ACA AAG TGG GTC CAG AAT GAT AAA TTT GCG TTT CAA AAA GAT      336
Cys Ile Thr Lys Trp Val Gln Asn Asp Lys Phe Ala Phe Gln Lys Asp
            100                 105                 110

GAT TTG ATT AAA TTT CAA CCA TCC ATT ATC GTT ATA TCA GAT AAC GCT      384
Asp Leu Ile Lys Phe Gln Pro Ser Ile Ile Val Ile Ser Asp Asn Ala
        115                 120                 125

GAT GAC GGA CAA AGT TCT ACT GAT AAA GAG AGT GAG ATT TCA ACT GAC      432
Asp Asp Gly Gln Ser Ser Thr Asp Lys Glu Ser Glu Ile Ser Thr Asp
130                 135                 140

GTA GAA AGT GAA AGG AAT GAT GAC AGC AAC AAT AAG GAT ATG ATA CAA      480
Val Glu Ser Glu Arg Asn Asp Asp Ser Asn Asn Lys Asp Met Ile Gln
145                 150                 155                 160

GCT TCA AAA CCT CTT AAG CGA CTT TTA CAG GAG GAT AAA GGA AGA GCT      528
Ala Ser Lys Pro Leu Lys Arg Leu Leu Gln Glu Asp Lys Gly Arg Ala
                165                 170                 175

TCC CTT GTT ACT GAC AAA ACG AAG TAC AAA AAC AAT GAA TTG ATT ATC      576
Ser Leu Val Thr Asp Lys Thr Lys Tyr Lys Asn Asn Glu Leu Ile Ile
            180                 185                 190

GGA GCG TTG AAA AGG TTA ACA AAA AAA TAT GAG ATC GAA GGT GAG AAA      624
Gly Ala Leu Lys Arg Leu Thr Lys Lys Tyr Glu Ile Glu Gly Glu Lys
        195                 200                 205

TTT CGT GCA AGA AGT TAT AGA CTG GCT AAA CAG TCG ATG GAA AAT TGC      672
Phe Arg Ala Arg Ser Tyr Arg Leu Ala Lys Gln Ser Met Glu Asn Cys
210                 215                 220

GAT TTC AAT GTT CGT TCC GGT GAA GAA GCA CAT ACT AAA TTA AGG AAT      720
Asp Phe Asn Val Arg Ser Gly Glu Glu Ala His Thr Lys Leu Arg Asn
225                 230                 235                 240

ATC GGG CCT AGT ATT GCC AAA AAA ATA CAA GTT ATA TTA GAT ACG GGA      768
Ile Gly Pro Ser Ile Ala Lys Lys Ile Gln Val Ile Leu Asp Thr Gly
                245                 250                 255

GTT TTA CCA GGT TTA AAT GAT TCA GTG GGA TTA GAA GAC AAG TTA AAA      816
Val Leu Pro Gly Leu Asn Asp Ser Val Gly Leu Glu Asp Lys Leu Lys
            260                 265                 270

TAC TTC AAA AAT TGT TAC GGC ATT GGG TCG GAA ATT GCT AAA CGC TGG      864
Tyr Phe Lys Asn Cys Tyr Gly Ile Gly Ser Glu Ile Ala Lys Arg Trp
        275                 280                 285

AAT CTT CTA AAT TTT GAA AGC TTT TGT GTT GCA GCT AAG AAG GAT CCA      912
Asn Leu Leu Asn Phe Glu Ser Phe Cys Val Ala Ala Lys Lys Asp Pro
    290                 295                 300

GAG GAG TTT GTA TCA GAT TGG ACA ATT TTA TTT GGT TGG TCA TAT TAC      960
Glu Glu Phe Val Ser Asp Trp Thr Ile Leu Phe Gly Trp Ser Tyr Tyr
305                 310                 315                 320

GAC GAT TGG TTA TGC AAG ATG TCT CGG AAT GAA TGT TTC ACA CAT TTA     1008
Asp Asp Trp Leu Cys Lys Met Ser Arg Asn Glu Cys Phe Thr His Leu
                325                 330                 335

AAG AAG GTT CAA AAA GCG CTG CGT GGC ATT GAT CCT GAA TGC CAA GTC     1056
Lys Lys Val Gln Lys Ala Leu Arg Gly Ile Asp Pro Glu Cys Gln Val
            340                 345                 350

GAA TTA CAG GGA AGT TAT AAT AGG GGC TAT TCC AAG TGT GGT GAC ATT     1104
Glu Leu Gln Gly Ser Tyr Asn Arg Gly Tyr Ser Lys Cys Gly Asp Ile
        355                 360                 365

GAT CTT TTA TTT TTC AAG CCG TTT TGT AAT GAC ACG ACC GAG TTG GCA     1152
Asp Leu Leu Phe Phe Lys Pro Phe Cys Asn Asp Thr Thr Glu Leu Ala
    370                 375                 380

AAA ATC ATG GAA ACG CTT TGT ATT AAG TTG TAC AAG GAT GGC TAT ATC     1200
Lys Ile Met Glu Thr Leu Cys Ile Lys Leu Tyr Lys Asp Gly Tyr Ile
385                 390                 395                 400

CAT TGT TTT TTA CAG CTA ACG CCA AAC TTG GAA AAG CTA TTC TTA AAA     1248
His Cys Phe Leu Gln Leu Thr Pro Asn Leu Glu Lys Leu Phe Leu Lys
                405                 410                 415
```

```
AGA ATA GTG GAG AGA TTT CGT ACA GCG AAG ATT GTT GGG TAT GGA GAA    1296
Arg Ile Val Glu Arg Phe Arg Thr Ala Lys Ile Val Gly Tyr Gly Glu
            420                 425                 430

AGA AAG AGG TGG TAT TCT TCT GAG ATA ATC AAG AAA TTT TTC ATG GGA    1344
Arg Lys Arg Trp Tyr Ser Ser Glu Ile Ile Lys Lys Phe Phe Met Gly
                435                 440                 445

GTC AAA TTC TCT CCA AGA GAA TTA GAA GAA CTG AAA GAA ATG AAA AAT    1392
Val Lys Phe Ser Pro Arg Glu Leu Glu Glu Leu Lys Glu Met Lys Asn
        450                 455                 460

GAT GAA GGC ACA TTG TTA ATT GAA GAA GAA GAA GAA GAA ACA AAA        1440
Asp Glu Gly Thr Leu Leu Ile Glu Glu Glu Glu Glu Glu Thr Lys
465                 470                 475                 480

TTA AAC CCG ATT GAC CAA TAT ATG TCT CTG AAT GCC AAG GAT GGA AAT    1488
Leu Asn Pro Ile Asp Gln Tyr Met Ser Leu Asn Ala Lys Asp Gly Asn
                485                 490                 495

TAT TGC AGA AGA TTA GAC TTT TTT TGT TGC AAG TGG GAT GAG CTT GGA    1536
Tyr Cys Arg Arg Leu Asp Phe Phe Cys Cys Lys Trp Asp Glu Leu Gly
            500                 505                 510

GCA GGA AGA ATA CAC TAT ACT GGA TCT AAA GAG TAC AAT AGA TGG ATA    1584
Ala Gly Arg Ile His Tyr Thr Gly Ser Lys Glu Tyr Asn Arg Trp Ile
        515                 520                 525

AGA ATA TTG GCA GCG CAA AAA GGC TTC AAG CTT ACA CAA CAC GGT TTA    1632
Arg Ile Leu Ala Ala Gln Lys Gly Phe Lys Leu Thr Gln His Gly Leu
530                 535                 540

TTT CGA AAT AAT ATC CTT CTC GAA AGC TTT AAC GAA CGC AGA ATT TTC    1680
Phe Arg Asn Asn Ile Leu Leu Glu Ser Phe Asn Glu Arg Arg Ile Phe
545                 550                 555                 560

GAG TTA TTA AAC TTA AAA TAC GCT GAA CCC GAA CAT AGA AAT ATC GAA    1728
Glu Leu Leu Asn Leu Lys Tyr Ala Glu Pro Glu His Arg Asn Ile Glu
                565                 570                 575

TGG GAA AAA AAA ACT GCA TAAAGGCATT                                 1756
Trp Glu Lys Lys Thr Ala
            580
```

(2) INFORMATION FOR SEQ ID NO:2:

(i) SEQUENCE CHARACTERISTICS:
        (A) LENGTH: 582 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Leu Lys Gly Lys Phe Ala Phe Leu Pro Asn Pro Asn Thr
1               5                   10                  15

Ser Ser Asn Lys Phe Phe Lys Ser Ile Leu Glu Lys Lys Gly Ala Thr
                20                  25                  30

Ile Val Ser Ser Ile Gln Asn Cys Leu Gln Ser Ser Arg Lys Glu Val
            35                  40                  45

Ile Ile Leu Ile Glu Asp Ser Phe Val Asp Ser Asp Met His Leu Thr
        50                  55                  60

Gln Lys Asp Ile Phe Gln Arg Glu Ala Gly Leu Asn Asp Val Asp Glu
65                  70                  75                  80

Phe Leu Gly Lys Ile Glu Gln Ser Gly Ile Gln Cys Val Lys Thr Ser
                85                  90                  95

Cys Ile Thr Lys Trp Val Gln Asn Asp Lys Phe Ala Phe Gln Lys Asp
            100                 105                 110
```

-continued

```
Asp Leu Ile Lys Phe Gln Pro Ser Ile Ile Val Ile Ser Asp Asn Ala
        115                 120                 125
Asp Asp Gly Gln Ser Ser Thr Asp Lys Glu Ser Glu Ile Ser Thr Asp
130                 135                 140
Val Glu Ser Glu Arg Asn Asp Asp Ser Asn Asn Lys Asp Met Ile Gln
145                 150                 155                 160
Ala Ser Lys Pro Leu Lys Arg Leu Leu Gln Asp Lys Gly Arg Ala
                165                 170                 175
Ser Leu Val Thr Asp Lys Thr Lys Tyr Lys Asn Asn Glu Leu Ile Ile
                180                 185                 190
Gly Ala Leu Lys Arg Leu Thr Lys Lys Tyr Glu Ile Glu Gly Glu Lys
                195                 200                 205
Phe Arg Ala Arg Ser Tyr Arg Leu Ala Lys Gln Ser Met Glu Asn Cys
            210                 215                 220
Asp Phe Asn Val Arg Ser Gly Glu Glu Ala His Thr Lys Leu Arg Asn
225                 230                 235                 240
Ile Gly Pro Ser Ile Ala Lys Lys Ile Gln Val Ile Leu Asp Thr Gly
                245                 250                 255
Val Leu Pro Gly Leu Asn Asp Ser Val Gly Leu Glu Asp Lys Leu Lys
                260                 265                 270
Tyr Phe Lys Asn Cys Tyr Gly Ile Gly Ser Glu Ile Ala Lys Arg Trp
            275                 280                 285
Asn Leu Leu Asn Phe Glu Ser Phe Cys Val Ala Ala Lys Lys Asp Pro
290                 295                 300
Glu Glu Phe Val Ser Asp Trp Thr Ile Leu Phe Gly Trp Ser Tyr Tyr
305                 310                 315                 320
Asp Asp Trp Leu Cys Lys Met Ser Arg Asn Glu Cys Phe Thr His Leu
                325                 330                 335
Lys Lys Val Gln Lys Ala Leu Arg Gly Ile Asp Pro Glu Cys Gln Val
                340                 345                 350
Glu Leu Gln Gly Ser Tyr Asn Arg Gly Tyr Ser Lys Cys Gly Asp Ile
            355                 360                 365
Asp Leu Leu Phe Phe Lys Pro Phe Cys Asn Asp Thr Thr Glu Leu Ala
370                 375                 380
Lys Ile Met Glu Thr Leu Cys Ile Lys Leu Tyr Lys Asp Gly Tyr Ile
385                 390                 395                 400
His Cys Phe Leu Gln Leu Thr Pro Asn Leu Glu Lys Leu Phe Leu Lys
            405                 410                 415
Arg Ile Val Glu Arg Phe Arg Thr Ala Lys Ile Val Gly Tyr Gly Glu
            420                 425                 430
Arg Lys Arg Trp Tyr Ser Ser Glu Ile Ile Lys Lys Phe Phe Met Gly
        435                 440                 445
Val Lys Phe Ser Pro Arg Glu Leu Glu Leu Lys Glu Met Lys Asn
            450                 455                 460
Asp Glu Gly Thr Leu Leu Ile Glu Glu Glu Glu Glu Thr Lys
465                 470                 475                 480
Leu Asn Pro Ile Asp Gln Tyr Met Ser Leu Asn Ala Lys Asp Gly Asn
                485                 490                 495
Tyr Cys Arg Arg Leu Asp Phe Cys Cys Lys Trp Asp Glu Leu Gly
            500                 505                 510
Ala Gly Arg Ile His Tyr Thr Gly Ser Leu Glu Tyr Asn Arg Trp Ile
            515                 520                 525
```

```
Arg Ile Leu Ala Ala Gln Lys Gly Phe Lys Leu Thr Gln His Gly Leu
    530                 535                 540

Phe Arg Asn Asn Ile Leu Leu Glu Ser Phe Asn Glu Arg Arg Ile Phe
545                 550                 555                 560

Glu Leu Leu Asn Leu Lys Tyr Ala Glu Pro Glu His Arg Asn Ile Glu
                565                 570                 575

Trp Glu Lys Lys Thr Ala
            580
```

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:3:

```
Met Tyr Pro Tyr Asp Val Pro Asp Tyr Ala Ser Leu
1               5                   10
```

(2) INFORMATION FOR SEQ ID NO:4:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:4:

```
TTTACCCTTT AGAGAAGGAC CACCCAAGCT AGCGTAGTCT GGGACGTCGT ATGGGTACAT      60

GAATTCATTG TCTAACAGGT C                                                81
```

(2) INFORMATION FOR SEQ ID NO:5:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO:5:

```
GGTGTCACTG ACAAGATCTC CCATGTCTCT ACTGGTGGTG CTTCTTTGGT AGCAGCACGC      60

CATAGTGACT GACG                                                        74
```

(2) INFORMATION FOR SEQ ID NO:6:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO:6:

```
GTAATAAGTA AAGGATAAAC ATGCGACCTG TTAGACAAAT CGCACTCATG TTTGACAGCT      60

TATCATC                                                                67
```

(2) INFORMATION FOR SEQ ID NO:7:

(i) SEQUENCE CHARACTERISTICS:
        (A) LENGTH: 29 base pairs
        (B) TYPE: nucleic acid -continued

```
        (C) STRANDEDNESS: single
        (D) TOPOLOGY: linear (xi) SEQUENCE DESCRIPTION: SEQ ID NO:7:

GAATTCTATC TCCGTAATCG GTCTCGGTC                                              29

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

AATAGCTTGG CAGCAACAGG G                                                      21

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

GAATTCCCAT GTCTCTACTG GTGGTGGTGC                                             30
```